United States Patent [19]
Tapscott et al.

[11] Patent Number: 5,352,595
[45] Date of Patent: Oct. 4, 1994

[54] MYOD REGULATORY REGION

[75] Inventors: Stephen J. Tapscott; Harold M. Weintraub, both of Seattle; Theodore D. Palmer, Kirkland, all of Wash.

[73] Assignee: Fred Hutchinson Cancer Research Center, Seattle, Wash.

[21] Appl. No.: 753,520

[22] Filed: Sep. 3, 1991

[51] Int. Cl.$^5$ .................... C12N 5/10; C12N 15/11; C12N 15/85
[52] U.S. Cl. ............... 435/172.3; 435/240.2; 435/320.1; 536/24.1
[58] Field of Search ............ 435/172.3, 240.2, 320.1; 536/27, 24.1

[56] References Cited

FOREIGN PATENT DOCUMENTS

90/15863 12/1990 World Int. Prop. O. ..... C12N 5/00

OTHER PUBLICATIONS

Johnson et al. (1989), Nucl. Acids Res. 17(19):7985–7986.
Chen et al. (1989), Genomics 4:479–497.
Lawrence et al. (Jan. 1990), J. Virol. 64(1):287–299.
Wiginton et al. (1986), Biochemistry 25(25):8234–8244.
McGeoch (1988), J. Gen. Virol. 69:1531–1574.
de Zamaroczy et al. (1986), Gene 47:155–177.
Pritchard et al. (1990), Nucl. Acids Res. 18(1):173–180.
Lassar, A. B. et al. 1989. Cell 58: 823.
Davis, R. L. et al. 1987. Cell 51: 987.
Wright, W. E. et al. 1989. Cell 56: 607.
Edmonson, D. G. et al. 1989. Genes Dev. 3: 628.
Braun, T. et al. 1989. EMJO J. 8: 701.
Rhodes, S. J. et al. 1989. Genes Dev. 3: 2050.
Miner, J. H. et al. 1990. Proc. Natl. Acad. Sci. USA 87: 1089.
Braun, T. et al. 1990, EMBO J. 9: 821.
Weintraub, H. R. et al. 1990. Proc. Natl. Acad. Sci. USA 87: 5623.
Piette, J. et al. 1990. Nature 345: 353.
Rosenthal, N. et al. 1990. Nucleic Acids Res. 18: 6239.
Sartorelli, V. 1990. Genes Dev. 4: 1811.
Murre, C. et al. 1989. Cell 58:537.
Brennan, T. J. 1990. Genes Dev. 4: 582.
Davis, R. L. et al. Cell 60: 733.
Sun, X. H. et al. 1991. Cell 64: 459.
Henthorn, P. et al. 1990. Science 247: 467–470.
Blackwell, T. K. et al. 1990. Science 250: 1104.
Schafer, B. W. et al. 1990. Nature 344: 454.
Benezra, R. et al. 1990. Cell 61: 49–59.
Lassar, A. B. et al. 1989. Cell 58: 659.
Sasson, D. et al. 1989. Nature 341: 303.
Crescerz, M. et al. 1990. Proc. Natl. Acad. Sci. USA 87: 8442.
Weintraub, H. et al. 1989. Proc. Natl. Acad. Sci. USA 86: 5434.
Choi, J. et al. 1990. Proc. Natl. Acad. Sci. USA 87: 7988.
Thayer, M. et al. 1990. Cell 63: 23.
Ptashne, M. et al. 1990. Nature 346: 329.
Lin, A. Y. et al. 1989. Gene Dev. 3: 986.
Stockschaleder, M. et al. 1991. Human Gene Therapy 2: 33–39.
Weintraub, H. et al. 1990. Science 251: 761.
Tabscott, S. J. et al. 1991. J. Clin. Invest. 87: 1133.

*Primary Examiner*—Richard A. Schwartz
*Assistant Examiner*—Philip W. Carter
*Attorney, Agent, or Firm*—Christensen, O'Connor, Johnson & Kindness

[57] ABSTRACT

Isolated DNA or RNA molecules capable of hybridizing under stringent conditions to the myoD regulatory region, its proximal promoter and distal enhancer regulatory regions, and regulatory elements within the proximal and distal regions for binding basic helix-loop-helix proteins, MyoD, and proteins binding at SP1, AP1, CAAT, M-CAT, CArG, and MEF sites in DNA. DNA or RNA expression vectors for introducing a gene into a cell under the regulatory control of the myoD regulatory region. Transduced or transfected pre-muscle cells, myocytes, or myoblasts. Methods of inducing a muscle phenotype in a non-muscle cell, positively selecting for a cells expressing MyoD, and negatively selecting for cells expressing MyoD.

13 Claims, 24 Drawing Sheets

FIGURE 1A
MYO D GENOMIC

```
TCTAGAAGCA TTCCANGTTC ACTCAGAGCA AGATGGNAAC CCATAGCACA GGTTTCTTC    60
TTCTCGGCAG AAACAGATCA ACCTAGACCC CCATGGGTCT CNTAGACACT CACAGAAAGT   120
AAGTTGGAGG GAGCCTCCCT CTCTCTCCCT CCCTCTTTTC CTTGGACTGT CCACCCGGAG   180
TTTGAGCAGA ATGGCTTGAA GTTTTAATGA TGATTCCCAC TACGCATGCA AGGACAGCGC   240
TGGGTTCTAA GCTTCCCGTG GAAGAACAGA TATTCTCTGA GCCATTCCCA GATGGAGAAT   300
GACCAAATAG CACTGCCACC GATCATTTGT GCCAGGCTTG CTCACCTAGA CCTTCTGAGT   360
CTCACTGTCT CTTGCCCACT TTGTCCTTGG CTCAACTTCT CTGGGTGTGT CATCATTTCT   420
CCACTCTTCT CTAGAACTTT CATTGTCCCG TAGCCTTGAG TCTCTCTCCA AACCTCCTGC   480
AATCTGATTT CTAACTCCTA TGCTTTTGCCT GGTCTCCAGA GTGGAGTCCG AGGTCAGCTC   540
CGAAGTGAGC ACTGAGGTCA GTACAGGCTG GAGGAGTAGA CACTGGAGAG GCTTGGGCAG   600
GCTGCACCAG ATAGCCAAGT GCTACCGCGT ATGGCTGCCA GTCTCTCTGC CCTCCTTCCT   660
AGCTAGGCAG CTGCCCCCAG ACAGAGTCGC GGGAGGGGGC ACTCCCTGGC CCAGTGGCT    720
ACCCTGGGGA CCCCAAGCTC CGCCCTACTA CACTCCTATT GGCTTGAGGC GCCCCGCC    780
CCAGCCCTCC TTTCCAGCTC CCGGGCTTTT AGGCTACCCT GGATAAATAG CCCAGGGCGC   840
CTGGCGCGAA GCTAGGGGCC AGGACGCCCC AGGACACGAC TGCTTTTCTTC ACCACTCCTC   900
TGACAGGACA GGACAGGGAG GAGGGGTAGA GGACAGCCGG AGTGGCAGAA AACCCACAGA   960
ACCTTTGTCA TGTACTGTT GGGGTTCCGG AGGAACTGGG ATATGGAGCT TCTATGCCGG ACTCTCACGG  1020
CTTGGGTTGA GGCTGGACCC AGGAACTGGG AGGCTCTC TCTGCTCCTT TGAGACAGCA CCACTCCGGG  1080
ACATAGACTT GACAGGCCCC GACGGCTCTC TGCGCTTTT TGAGGACCTG GACCCGCGCC GACGACTTCT  1140
ATGATGACCC GTGTTTCGAC TCACCAGACC CTGAAAACCGG AGGAGCACGC ACACTTCCCT ACTGCGGTGC  1200
TGGTGCACAT GGGAGCCCTC CTGAAAACCGG GAGGATGAGC ATGTGCGCGC GCCCAGCGGG CACCACCAGG  1260
ACCCAGGCCC AGGCGCTCGT GAGGATGAGC GCCTGCAAGG CGTGCAAGCG CAAGACCACC AACGCTGATC  1320
CGGGTCGCTG CTTGCTGTGG GCCTGCAAGG CGCGAGCGCC GCCGCCTGAG CAAAGTGAAT GAGGCCTTCG  1380
GCCGCAAGGC CGCACCATG CGCGAGCGCC TCCAGCAACC CGAACCAGCG GCTACCCAAG GTGGAGATCC   1440
AGACGCTCAA GCGCTGCACG CGAACCAGCG                                              1500
```

FIGURE 1B

```
TGCGCAACGC CATCCGCTAC ATCGAAGGTC TGCAGGCTCT GCTGCGCGAC CAGGACGCCG 1560
CGCCCCCTGG CGCCGCTGCC TTCTACGCAC CTGGACCGCT GCCCCCAGGC CGTGGCAGCG 1620
AGCACTACAG TGGCGACTCA GACGCGTCCA GCCCGCGCTC CAACTGCTCT GATGGCATGG 1680
TAAGGCGGGG GGCTCAGGAG GACGAGCAAT GGAGGCGGCG CCTGGGGTAT CTGCAACAGG 1740
TTTCCGAGGC CCTTGGGGTG GGGTGTCCC TTATACCTAG ATGCTCCTGG CATCTGACAC 1800
TGGAGTCGCT TTGGAGACCC ATGGCATCT ATGATNCTGC CGATCGGGGG TGGAACACTG 1860
CTGCGCAGAC CCCGGGATAT GCTTTTCCTT CTCATTATTA CCCTAATGTC AGATTGATTG 1920
TTTCCTGGAG TGACTGTCCA CTCTCAGTTT GGCCCCGCAT GCGACAGCTT CCAGTGTGTG 1980
GCTGGGTCCT ACCACCTGGG GAGCTGACCC AGTCCTGGAA CCAGCAGCTG AGACTAAGGG 2040
AGTGAGGGAG GGGTGATGAC AAGGAGTGTT GCTTGAGACC CACTCGGGCC CTGTAGACCT 2100
AACTCTGTTA TCCTTGCTAT TCGCAGATGG ATTACAGCGG CCCCCCAAGC GGCCCCCGGC 2160
GGCAGAATGG CTACGACACC GCCTACTACA GTGAGGCGGC GCGCGGTGCG TATTCTCAGC 2220
TGTTCCCAGC TAGCAGGCCT TATCGGCNTT CTGTATCCCC CTTGAAACTT TCCTCGCTCC 2280
TAGGCTTAGT ATCCTTCCTC CTGCCTCACC ACATACATAC CCGTACCTTG GGATGGCGGG 2340
GGGGGGGGAG GCTGGGGGGG GAGCATTGGG GGAGGGCAAA GAACTATGAT GCACANTTCC 2400
TCTCCTTTCT CCTTCCAGTC TAGCAAGTCC TCAGTTTCCC TTTTCTACAA AGCTCCGTGC 2460
CTATGGGCAG GAGACTTGAG AAGGGCCGCA AGTTTGGATT ACTAACCTTC CACTCCCCTC 2520
ACAGAGTCCA GGCCAGGGAA GAGTGCGGCT GTGTCGAGCC TCGACTGCCT GTCCAGCATA 2580
GTGGAGCGCA TCTCCACAGA CAGCCCCGCT GCGCCTGCGC TGCTTTTGGC AGATGCACCA 2640
CCAGAGTCGC CTCCGGGTCC GCCAGAGGGG GCATCCCTAA GCGACACAGA ACAGGGAACC 2700
CAGACCCCGT CTCCCGACGC CGCCCCTCAG TGTCCTGCAG GCTCAAACCC CAATGCGATT 2760
CAGAGTGTGC TTTGAGAGAT CGACTGCAGC AGCAGAGGGC GCACCACCGT AGGCACTCCT 2820
TATCAGGTGG CCCCTGGTTC TTCACGCCCA AAAGATGAAG CTTAAATGAC ACTCTTCCCA 2880
GGGATGGTG CGAAGCCGTT CTTCCAGAGG GAAGGGAAGA GCAGAAGTCT GTCCTAGATC 2940
ACTGTCCTTT CGAAGCCGTT AGTCCTTTTT GTTGTTGTTG TTGTAGTCCT TCAGTTGTTT 3000
CAGCCCCAAA GAAAGGACAT AGTCCTTTTT GTTGTTGTTG TTGTAGTCCT TCAGTGTTT 3000
GTTGTTTTT TCATGCGGCT CACAGCGAAG GCCACTTGCA CTCTGGCTGC ACCTCACTGG 3060
```

FIGURE 1C

| | | | | | |
|---|---|---|---|---|---|
| GCCAGAGCTG | ATCCTTGAGT | GGCCAGGCGC | TCTTCCTTTC | CTCATAGCAC | AGGGGTGAGC | 3120
| CTTGCACACC | TAAGCCCTGC | CCTCCACATC | CTTTTGTTTG | TCACTTTCTG | GAGCCCTCCT | 3180
| GGCACCCACT | TTTCCCCACA | GCTTGCGGAG | GCCACTCAGG | TCTCAGGTGT | AACAGGTGTA | 3240
| ACCATACCCC | ACTCTCCCCC | TTCCCGCGGT | TCAGGACCAC | TTATTTTTTT | ATATAAGACT | 3300
| TTTGTAATCT | ATTCGTGTAA | ATAAGAGTTG | CTTGGCCAGA | GCGGGAGCCC | CTTGGGCTAT | 3360
| ATTTATCTCC | CAGGCATGCT | GTGTAGTGCA | ACAAAAACTT | TGTATGTTTA | TTCCTCAAGC | 3420
| GGGCGAGCCT | CGAGGCTCGC | TCGCTCAGGT | GTTGGAAATA | AAGACGCTAA | TTTATACAAA | 3480
| GTGGCTCTGG | CTTTTCCTAA | GGGGATCAGA | AAGAAACTCT | ACGAACTGGG | CGGGCTGTCT | 3540
| CGCAGCGACC | CCTGTAGGTG | GCAGAAGGGT | GCAGAAGGGT | CTGGGTAGTG | CTGGGTAATG | 3600
| AAGAAAGGGCT | GGCAGACCTC | CAGCTGTAGG | GAATTC 3636 | | |

*CM—CHICK MUSCLE CELL TRANSIENT TRANSFECTANTS, EXPERIMENTAL
**CF— CHICK FIBROBLAST TRANSIENT TRANSFECTANTS, CONTROL

FIGURE 4A
KX FRAG MYOD ENHANCER

```
GGGCCCAGCC ACCAGGATGG TATAGTATAG NATAGATTTT ATTTAGAGCA TAGGGAGGGG    60
AGTCAAGAGG GCAGTAGAGG CAAAGAAAGG AAGAGAGAGG GGGAGAGAAG AGAAGTAGAG   120
GTGTAGAGGC TGGCCTTGGA GCACGTGGAG AGAGCAGGGN AAAGGAATGG GGAGAGAGGG   180
NAGAATTGGA AACAGAGAAA GAGCAAGAGA GGATCAAGAG AGCAAGGAGG GGGCAAGCA    240
GCCCNTTTTA TAGTGAGTCA GGCACACCTG GTTGTTGCCA GGTAACTGTG GGGCGGGGNT   300
TAGACACAAA GCTAAAAACA TCCACCACCT AGTTNATCTG CCAGACTCTC AAGGTCCTCG   360
CATACCAGAG CCTGGGGAA TCCCAGAGGG AGACATGTGA AGGCTCCCTG GGACCCTGGT    420
CAGGACNGGA CCATGTCTGT GCCCAGCCNG AGTTCCTCTA GGTCAGCCTA AATTGGCCAG   480
ATCTACACTT GGTGGCAGGC AGTTTCAGGC TTTCTGGGAA GCAAAACTGG CAGAGAACAG   540
AGCAGGATCC TTGAGTTGGG AAAGGAAAGT CTAGGGCCAG AGACTGAACC TGGGCTGGT    600
CCTGTTCCAC CTGTNCTCCC NGTGGTTTCA TCCTCCAGTC CTTCAGCCCC CTAGACCCAA   660
GCCAGCCATG CAGCCCCGCA TAGCAAAGTA AGAGGCCACA GGTCCAGAGT GGTAGGGCA    720
GAGGTGCCTG AGGCTTGGGG CAGGTGCTAG TTGGATCCGG TTTCCAGAGG CAATATATAT   780
ATAAAGGCTG CTGTTTCCCC GATGGTGCAA CACCCCAGAG GCCTAGCCAG ACCAACATTC   840
CTGCCNAAAA GCCAGCTCTC CATTTATAGC ACCTTGGAAG ACTAGCCAAG GGAGCTGAAA   900
TGCAAGGCCT GGAAAGGACA GGGGAAATC AAAGGGCCAC CTATGGCGGC AGGAGAACTG   960
AGCCTCAGGA TGAGCTGTGT GCTTCTCCAG GTCAGTGGGC CTACAGCCTA AGAGGCCCTG  1020
CATTGAGGGG ACAATGCCTC AGCCCAGAGC CAATGGCACG CTCCAGAAGG GGTGGCTGGG  1080
GGAAGTTTTA GTGACCATAA AAGGTTGCAA AAGGTTGCAA TCAGCATAAA TCACTTAGAC  1140
ATTTATTTCG GTTTTTNTAA ATTATTCGTT TTGTTATTTG TGTGCTTGCT TTGCTTTGCT  1200
TTGTTTGCTC GGGTTTGAGA TAAGAGAGAG AGAGAGAGAG AGAGAGGGAA AGAGAGGGAA  1260
GGAGGGAGGG AGGGAGGGAG GGAGGGAGGG AGGAAGGAAG GAAGGAAGGA AGGAAGGAAG  1320
```

FIGURE 4B

```
AAAGAAAGAA AGAAAGAAAG AAAGAAAGAA AGAAAGAAAG AAAGAAAGAA ACTAGATTTG 1380
CACAAGTGGT TTGAAGTGCC TTCCTTGGAG ACACCAGGCA CTGCATAATG AAACAGACTT 1440
GCTCATTCAT CNGCCGAAGG AATATTTGTG GTGCACCTAG AGAGAGCTGA GCATATTCAG 1500
CTGAGGTTCC AAAAAGGAGG AAGCAATAGC TTCGATCGAA ATCATTACTA ACGACAATTA 1560
CATCCATCNC TGTAGATTTA AGTCAAATGA AAGAGCACTT ATGATGAACC CCACATCCAT 1620
CGGCAGCATA CTGTTGGAAT GTTGCAACCG ACCAATGGGA GAGAGCACGT CCCAGGCAAA 1680
CCAGCCTCTG CTTTGCCTGG GCAGAGGCAG CGTGAGAGCT TGTATGAGTA AGTACCTACA 1740
TAGAGCCCAG GTTTGCTGGA ATAGAATGAC TTGTAGCACA TTTTGCTAAA TTCAAGTATA 1800
AGGATAGAAA TCAAAAGAGC CCAAGACTCT TCATTCACTC GCTTCACACT TAAACCACTG 1860
TGCCCGCCGT GGGATCACTG CTGCAGTGGC TTCCGGACAC GCCATGGTGA GCAAAGTACT 1920
CCTATCCATG GTATGCTCTGGT CTTCGTGTCC CTCGGTGATA ACTGACAAGA TCATTCTC 1978
```

FIGURE 7A
pLHDMDN-531, LTR HIS D, MYO-D 531.4 APAI FRAGMENT DRIVING NEO.
LTR

```
GAATTGCTAG CAATTGCTAG CAATTGCTAG CAATTCATAC CAGATCACCG AAAACT
GTCCTCCAAA TGTGTCCCCC TCACACTCCC AAATTCGCGG GCTTCTGCCT CTTAGACCAC
TCTACCCTAT TCCCCACACT CACCGGAGCC AAAGCCGCGG CCCTTCCGTT TCTTTGCTTT
TGAAAGACCC CACCCGTAGG TGGCAAGCTA GCTTAAGTAA CGCCACTTTG CAAGGCATGG
AAAAATACAT AACTGAGAAT AGGAAAGTTC AGATCAAGGT CAGGAACAAA GAAACAGCTG
AATACCAAAC AGGATATCTG TGGTAAGCGG TTCCTGCCCC GGCTCAGGGC CAAGAACAGA
TGAGACAGCT GAGTGATGGG CCAAACAGGA TATCTGTGGT AAGCAGTTCC TGCCCCGGCT
CGGGGCCAAG AACAGATGGT CCCCAGAGC TATCTGTGTT CCTGTACCTT CTAGTGAATC
ATCAGATGTT TCCAGGGTGC CCCAAGGACC TGAAAAATGAC CCTGTACCTT ATTTGAACTA
ACCAATCAGT TCGCTTCTCG CGCGCGCCAGT CGCGCTTCCG CTCTCCGAGC TCAATAAAAG
AGCCCACAAC CCCTCACTCG GCGCGCCAGT ACTGCGTCGC CCGGGTACCC
GTATTCCCAA TAAAGCCTCT TGCTGTTTGC ATCCGAATCG TGGTCTCGCT GTTCCTTGGG
AGGGTCTCCT CTGAGTGATT GACTACCCAC GACGGGGGTC TTTCATTTGG GGGCTCGTCC
GGGATTTGGA GACCCCTGCC CAGGGACCAC CGACCCACCA CCGGGAGGTA AGCTGGCCAG
CAACTTATCT GTGTCTGTCC GATTGTCTAG TGTCTATGTT TGATGTTATG CGCCTGCGTC
TGTACTAGTT AGCTAACTAG CTCTGTATCT GGCGGACCCG TGGTGGAACT GACGAGTTCT
GAACACCCGG CCGCAACCCT GGGAGACGTC CCAGGGACTT TGGGGCCGT TTTGTGGCC
CGACCTGAGG AAGGGAGTCG ATGTGGAATC CGACCCCGTC AGGATATGTG GTTCTGGTAG
GAGACGAGAA CCTAAAACAG TTCCCGCCTC CGTCTGAATT TTTGCTTTCG GTTTGGAACC
GAAGCCGCGC GTCTTGTCTG CTG
```

```
CAGCATCGTT CTGTGTTGTC TCTGTCTGAC TGTGT
TTCTGTATTT GTCTGAAAAT TAGGGCCAGA CTGTTACCAC TCCCTTAAGT TTGACCTTAG
GTCACTGGAA AGATGTCGAG CGGATCGCTC ACAACCAGTC GGTAGATGTC AAGAAGAGAC
GTTGGGTTAC CTTCTGCTCT GCAGAATGGC CAACCTTTAA CGTCGGATGG CCGCGAGACG
GCACCTTTAA CCGAGACCTC ATCACCCAGG TTAAGATCAA GGTCTTTTCA CCTGGCCCGC
ATGGACACCC AGACCAGGTC CCCTACATCG TGACCTGGGA AGCCTTGGCT TTTGACCCCC
CTCCCTGGGT CAAGCCCTTT GTACACCCTA AGCCTCCGCC TCCTCTTCCT CCATCCGCCC
CGTCTCTCCC CCTTGAACCT CCTCGTTCGA CCCCGCCCTCG ATCCTCCCTT TATCCAGCCC
TCACTCCTTC TCTAGGCGCC GGAATT
```

HIS D

```
GATCCCGGAC CATGAGCTTC AATACCCTGA TTG
ACTGGAACAG CTGTAGCCCT GAACAGCAGC GTGCGCTGCT GACGGCGTCCG GCGATTTCCG
CCCTCTGACAG TATTACCCGG ACGGTCAGCG ATATTCTGGA TAATGTAAAA ACGGCGCGGTG
ACGATGCCCT GCGTGAATAC AGCGCTAAAT TTGATAAAAC AGAAGTGACA GCGCTACGCG
TCACCCCTGA AGAGATCGCC GCCGCCGGCG CGCGTCTGAG CGACGAATTA AAACAGGCGA
TGACCGCTGC CGTCAAAAAT ATTGAAACGT TCCATTCCGC GCAGACGCTA CCGCCTGTAG
ATGTGGAAAC CCAGCCAGGC GTGCGTTGCC AGCAGGTTAC GCGTCCCGTC TCGTCTGTCG
GTCTGTATAT TCCCCGGCGG TCGGCTCCGC TCTTCTCAAC GGTGCTGATG CTGGCGACGC
CGGCGCGCAT TGCGGCGCAA CAGAAGGTGG TTCTGTGCTC GCCGCCGCCC ATCGCTGATG
AAATCCTCTA TGCGGCGCAA CTGTGTGGCG TGCAGGAAAT CTTTAACGTC GGCGGCGCGC
AGGCGATTGC CGCTCTGGCC TTCGGCAGCG AGTCCGTACC GAAAGTGGAT AAAATTTTTG
GCCCCGGCAA CGCCTTTGTA ACCGAAGCCA AACGTCAGGT CAGCCAGCGT CTCGACGGCG
CGGCTATCGA TATGCCAGCC GGGCCGTCTG AAGTACTGGT GATCGCAGAC AGCGGCGCAA
CACCGGGATTT CGTCGCTTCT GACCTGCTCT CCCAGGCTGA GCACGGCCCG GATTCCCAGG
TGATCCTGCT GACGCCTGAT GCTGACATTG CCCGCAAGGT GGCGGAGGCG GTAGAACGTC
```

FIGURE 7C
AACTGGCGGA ACTGCCGCGC GCGGACACCG CCCGGCAGGC CCTGAGCGCC AGTCGTCTGA
TTGTGACCAA AGATTAGCG CAGTGCGTCG CCATCTCTAA TCAGTATGGG CCGAACACT
TAATCATCCA GACGCGCAAT GCGCGCGATT TGGTGGATGC GATTACCAGC GCAGGCTCGG
TATTTCTCGG CGACTGGTCG CCGGAATCCG CCGGTGATTA CGCTTCCGGA ACCAACCATG
TTTTACCGAC CTATGGCTAT ACTGCTACCT GTTCCAGCCT TGGGTTAGCG GATTTCCAGA
AACGGATGAC CGTTCAGGAA CTGTCGAAAG CGGGCTTTTC CGCTCTGCCA TCAACCATTG
AAACATTGGC GGCGGCAGAA CGTCTGACCG CCCATAAAAA TGCCGTGACC CTGCGCGTAA
ACGCCCTCAA GGAGCAAGCA TGAGCACTGA AAACACTCTC AGCGTCGCCG GGATC

AATTCGTTAA CTCGAGGATC
531 MYO
GGCCCCAGCC ACCAGGATGG TATAGTATAG NATAGATTTT ATTTAGAGCA TAGGGAGGGG
AGTCAAGAGG GCAGTAGAGG CAAAGAAAAG AAGAGAGAGG GGGAGTAGAG AGAAGTAGAG
GTGTAGAGGC TGGCCTTGGA GCACGTGGAG AGAGCAGGGN AAAGGAATGG GGAGAGAGGG
NAGAATTGGA AACAGAGAAA GAGCAAGAGA GGATCAAGAG AGCAAGGAGG GGGCAAGCA
GCCCNTTTTA TAGTGAGTCA GGCACACCTG GTTGTTGCCA GGTAACTGTG GGGCGGGGNT
TAGACACAAA GCTAAAAACA TCCACCACCT AGTTNATCTG CCAGACTCTC AAGGTCCTCG
CATACCAGAG CCTGGGGGAA TCCCAGAGGG AGACATGTGA AGGCTCCCTG GGACCCTGGT
CAGGACNGGA CCATGTCTGT GCCCAGCCNG AGTTCCTCTA AGGTCAGCCTA AATTGGCCAG
ATCTACACTT GGTGGCAGGC AGTTTCAGGC TTTCTGGGAA GCAAAAACTGG CAGAGAACAG
AGCAGGATCC TTGAGTTGGG AAAGGAAAGT CTAGGGCCAG AGACTGAACC TGGGGCTGGT
CCTGTTCCAC CTGTNCTCCC NGTGGTTTCA TCCTCCAGTC CTTCAGCCCC CTAGACCCAA
GCCAGCCATG CAGCCCCGCA TAGCAAAGTA AGAGCCCACA GGTCCAGGACT GGGTAGGGCA
GAGGTGCCTG AGGCTTGGGG CAGGTGCTAG TTGGATCCGG TTTCCAGAGG CAATATATAT
ATAAAGGCTG CTGTTTCCCC GATGGTGCAA CACCCCAGAG GCCTAGCCAG ACCAACATTC
CTGCCNAAAA GCCAGCTCTC CATTTATAGC ACCTTGGAAG ACTAGCCAAG GGAGCTGAAA

FIGURE 7D

```
TGCAAGGCCT GGAAAGGACA GGGGGAAATC AAAGGGCCAC CTATGGCGGC AGGAGAACTG
AGCCTCAGGA TGAGCTGTGT GCTTCTCCAG GTCAGTGGGC CTACAGCCTA AGAGGCCCTG
CATTGAGGGG ACAATGCCCT AGCCCAGAGC CAATGGCACG CTCCAGAAGG GGTGGCTGGG
GGAAGTTTTA GTGACCATAA AATAAAAAGC AAGGTTGCAA TCACTTAGAC TCAGCATAAA
ATTTATTTCG GTTTTNTAA ATTATTCGTT TTGTTATTTG TGTGCTTGCT TTGCTTTGCT
TTGTTTGCTC GGGTTTGAGA TAAGAGAGAG AGAGAGAGAG AGAGAGAGAG AGAGAGGAA
GGAGGAGGG AGGGAGGAG GGAGGAGGG AGGAAGGAG GAAGGAAGGA AGGAAGGAAG
AAAGAAAGAA AGAAAGAAAG AAAGAAAGAA AGAAAGAAAG AAAGAAAGAA ACTAGATTTG
CACAAGTGGT TTGAAGTGCC TTCCTTGGAG ACACCAGCA CTGCATAATG AAACAGACTT
GCTCATTCAT CNGCCGAAGG AATATTTGTG GTGCACCTAG AGAGAGCTGA GCATATTCAG
CTGAGGTTCC AAAAAGGAGG AAGCAATAGC TTCGATCGAA ATCATTACTA ACGACAATTA
CATCCATCNC TGTAGATTTA AGTCAAATGA AAGAGCACTT ATGATGAACC CCACATCCAT
CGGCAGCATA CTGTTGGAAT GTTGCAACCG ACCAATGGGA GAGAGCACGT CCCAGGCAAA
CCAGCCTCTG CTTTGCCTGG GCAGAGGCAG CGTGAGAGCT TGTATGAGTA AGTACCTACA
TAGAGCCCAG GTTTGCTGGA ATAGAATGAC TTGTAGCACA TTTTGCTAAA TTCAAGTATA
AGGATAGAAA TCAAAAGAGC CCAAGACTGT TCATTCACTC GCTTGACACT TAAACCACTG
TGCCCGCCGT GGGATCACTG CTGCAGTGGC TTCCGGACAC GCCATGGTGA GCAAAGTACT
CCTATCCATG GTATGCTGGT CTTCGTGTCC CTCGGTGATA ACTGACAAGA TCATTCTCGA
GGTAGACACT GGAGAGGCTT GGGCAGGCTG CACCAGATAG CCAAGTGCTA CCGGCGTATGG
CTGCCAGTCT CTCTGCCCTC CTTCCTAGCT AGGCAGCTGC CCCAGCACAG AGTCGCGGGA
GGGGCACTC CCTGGCCCCA GTGGCTACCC TGGGGACCCC AAGCTCCGCC CTACTACACT
CCTATTGGCT TGAGGCGCCC CCGCCCCCAG CCTCCCTTTC CAGCTCCCCGG GCTTTTAGGC
TACCCTGGAT AAATAGCCCA G
NEO
AGCTT
GGGCTGCAGG TCGAGGCGGA TCT
```

FIGURE 7E

```
GATCAAGAGA CAGGATGAGG ATCGTTTCGC ATGATTGAAC AAGATGGATT GCACGCAGGT
TCTCCGGCCG CTTGGGTGGA GAGGCTATTC GGCTATGACT GGGCACAACA GACAATCGGC
TGCTCTGATG CCGCCGTGTT CCGGCTGTCA GCGCAGGGGC GCCCGGTTCT TTTTGTCAAG
ACCGACCTGT CCGGTGCCCT GAATGAACTG CAGGACGAGG CAGCGCGGCT ATCGTGGCTG
GCCACGACGG GCGTTCCTTG CGCAGCTGTG CTCGACGTTG TCACTGAAGC GGGAAGGGAC
TGGCTGCTAT TGGGCGAAGT GCCGGGGCAG GATCTCCTGT CATCTCACCT TGCTCCTGCC
GAGAAAGTAT CCATCATGGC TGATGCAATG CGGCGGCTGC ATACGCTTGA TCCGGCTACC
TGCCCATTCG ACCACCAAGC GAAACATCGC ATCGAGCGAG CACGTACTCG GATGGAAGCC
GGTCTTGTCG ATCAGGATGA TCTGGACGAA GAGCATCAGG GGCTCGCGCC AGCCGAACTG
TTCGCCAGGC TCAAGGCGCG CATGCCCGAC GGCGAGGATC TCGTCGTGAC CCATGGCGAT
GCCTGCTTGC CGAATATCAT GGTGGAAAAT GGCCGCTTTT CTGGATTCAT CGACTGTGGC
CGGCTGGGTG TGGCGGACCG CTATCAGGAC ATAGCGTTGG CTACCCGTGA TATTGCTGAA
GAGCTTGGCG GCGAATGGGC TGACCGCTTC CTCGTGCTTT ACGGTATCGC CGCTCCCGAT
TCGCAGCGCA TCGCCTTCTA TCGCCTTCTT GACGAGTTCT TCTGAGCGGG ACTCTGGGGT
TC

LTR

GATAAAATAA AAGATTTTAT TTAGTCT
CCAGAAAAAG GGGGGAATGA AAGACCCCAC CTGTAGGTTT GGCAAGCTAG CTTAAGTAAC
GCCATTTTGC AAGGCATGGA AAATACATA ACTGAGAATA GAGAAGTTCA GATCAAGGTC
AGGAACAGAT GGAACAGCTG AATATGGGCC AAACAGGATA TCTGTGGTAA GCAGTTCCTG
CCCCGGCTCA GGGCCAAGAA CAGATGGAAC AGCTGAATAT GGGCCAAACA GGATATCTGT
GGTAAGCAGT TCCTGCCCCG GCTCAGGGCC AAGAACAGAT GGTCCCCAGA TGCGGTCCAG
CCCTCAGCAG TTTCTAGAGA ACCATCAGAT GTTTCCAGGG TGCCCCAAGG ACCTGAAATG
ACCCTGTGCC TTATTTGAAC TAACCAATCA GTTCGCTTCT CGCTTCTGTT CGCGCGCTTC
TGCTCCCCGA GCTCAATAAA AGAGCCCACA ACCCCTCACT CGGG
GCGCCAGTCC TCCGATTGAC TGAGTCGCCC GGGTACCCGT GTATCCAATA AACCCTCTTG
```

FIGURE 7F

CAGTTGCATC CGACTTGTGG TCTCGCTGTT CCTTGGGAGG GTCTCCTCTG AGTGATTGAC
TACCCGTCAG CGGGGGTCTT TCATTTGGGG GCTCGTCCGG GATCGGGAGA CCCCTGCCCA
GGGACCACCG ACCCACCACC GGGAGGTAAG CTGG pBR322
CTGCCTCGCG CGTTTCGGTG ATGACGGTGA AAA
CCCTCTGACAC ATGCAGCTCC CGGAGACGGT CACAGCTTGT CTGTAAGCGG
ATGCCGGGAG CAGACAAGCC CGTCAGGGCG CGTCAGCGGG TGTTGGCGGG
TGTCGGGGCG CAGCCATGAC CCAGTCACGT AGCGATAGCG GAGTGTATAC
TGGCTTAACT ATGCGGCATC AGAGCAGATT GTACTGAGAG TGCACCATAT
GCGGTGTGAA ATACCGCACA GATGCGTAAG GAGAAAATAC CGCATCAGGC
GCTCTTCCGC TTCCTCGCTC ACTGACTCGC TGCGCTCGGT CGTTCGGCTG
CGGCGAGCGG TATCAGCTCA CTCAAAGGCG GTAATACGGT TATCCACAGA
ATCAGGGGAT AACGCAGGAA AGAACATGTG AGCAAAAGGC CAGCAAAAGG
CCAGGAACCG TAAAAAGGCC GCGTTGCTGG CGTTTTTCCA TAGGCTCCGC
CCCCCTGACG AGCATCACAA AAATCGACGC TCAAGTCAGA GGTGGCGAAA
CCCGACAGGA CTATAAAGAT ACCAGGCGTT TCCCCCTGGA AGCTCCCTCG
TGCGCTCTCC TGTTCCGACC CTGCCGCTTA CCGGATACCT GTCCGCCTTT
CTCCCTTCGG GAAGCGTGGC GCTTTCTCAT AGCTCACGCT GTAGGTATCT
CAGTTCGGTG TAGGTCGTTC GCTCCAAGCT GGGCTGTGTG CACGAACCCC
CCGTTCAGCC CGACCGCTGC GCCTTATCCG GTAACTATCG TCTTGAGTCC
AACCCGGTAA GACACGACTT ATCGCCACTG GCAGCAGCCA CTGGTAACAG
GATTAGCAGA GCGAGGTATG TAGGCGGTGC TACAGAGTTC TTGAAGTGGT
GGCCTAACTA CGGCTACACT AGAAGGACAG TATTTGGTAT CTGCGCTCTG
CTGAAGCCAG TTACCTTCGG AAAAAGAGTT GGTAGCTCTT GATCCGGCAA
ACAAACCACC GCTGGTAGCG GTGGTTTTTT TGTTTGCAAG CAGCAGATTA
CGCGCAGAAA AAAAGGATCT CAAGAAGATC CTTTGATCTT TTCTACGGGG

```
FIGURE 7G
TCTGACGCTC AGTGGAACGA AAACTCACGT TAAGGGATTT TGGTCATGAG
ATTATCAAAA AGGATCTTCA CCTAGATCCT TTTAAATTAA AAATGAAGTT
TTAAATCAAT CTAAAGTATA TATGAGTAAA CTTGGTCTGA CAGTTACCAA
TGCTTAATCA GTGAGGCACC TATCTCAGCG ATCTGTCTAT TTCGTTCATC
CATAGTTGCC TGACTCCCCG TCGTGTAGAT AACTACGATA CGGGAGGGCT
TACCATCTGG CCCCAGTGCT GCAATGATAC CGCGAGACCC ACGCTCACCG
GCTCCAGATT TATCAGCAAT AAACCAGCCA GCCGGAAGGG CCGAGCGCAG
AAGTGGTCCT GCAACTTTAT CCGCCTCCAT CCAGTCTATT AATTGTTGCC
GGGAAGCTAG AGTAAGTAGT TCGCCAGTTA ATAGTTTGCG CAACGTTGTT
GCCATTGCTG CAGGCATCGT GGTGTCACGC TCGTCGTTTG GTATGGCTTC
ATTCAGCTCC GGTTCCCAAC GATCAAGGCG AGTTACATGA TCCCCCATGT
TGTGCAAAAA AGCGGTTAGC TCCTTCGGTC CTCCGATCGT TGTCAGAAGT
AAGTTGGCCG CAGTGTTATC ACTCATGGTT ATGGCAGCAC TGCATAATTC
TCTTACTGTC ATGCCATCCG TAAGATGCTT TTCTGTGACT GGTGAGTACT
CAACCAAGTC ATTCTGAGAA TAGTGTATGC GGCGACCGAG TTGCTCTTGC
CCGGCGTCAA CACGGGATAA TACCGCGCCA CATAGCAGAA CTTTAAAAGT
GCTCATCATT GGAAAACGTT CTTCGGGGCG AAAACTCTCA AGGATCTTAC
CGCTGTTGAG ATCCAGTTCG ATGTAACCCA CTCGTGCACC CAACTGATCT
TCAGCATCTT TTACTTTCAC CAGCGTTTCT GGGTGAGCAA AAACAGGAAG
GCAAAATGCC GCAAAAAAGG GAATAAGGGC GACACGGAAA TGTTGAATAC
TCATACTCTT CCTTTTTCAA TATTATTGAA GCATTTATCA GGGTTATTGT
CTCATGAGCG GATACATATT TGAATGTATT TAGAAAAATA AACAAATAGG
GGTTCCGCGC ACATTTCCCC GAAAAGTGCC ACCTGACGTC TAAGAAACCA
TTATTATCAT GACATTAACC TATAAAAATA GGCGTATCAC GAGGCCCTTT
CGTCTTCAA
```

FIGURE 8A
pLHDMDN-NSA, LTR HisD, Myo-D NSA ApaI fragment driving neo.
LTR

```
GAATTGCTAG CAATTGCTAG CAATTGCTAG CAATTCATAC CAGATCACCG AAAACT
GTCCTCCAAA TGTGTCCCCC TCACACTCCC AAATTCGCGG GCTTCTGCCT CTTAGACCAC
TCTACCCTAT TCCCCACACT CACCGGAGCC AAAGCCGCGG CCCTTCCGTT TCTTTGCTTT
TGAAAGACCC CACCCGTAGG TGGCAAGCTA GCTTAAGTAA CGCCACTTTG CAAGGCATGG
AAAAATACAT AACTGAGAAT AGGAAAAGTT CAGATCAAGGT CAGGAACAAA GAAACAGCTG
AATACCAAAC AGGATATCTG TGGTAAGCGG TTCCTGCCCC GGCTCAGGGC CAAGAACAGA
TGAGACAGCT GAGTGATGGG CCAAACAGGA TATCTGTGGT AAGCAGTTCC TGCCCCGGCT
CGGGGCCAAG AACAGATGGT CCCCAGATGC GGTCCAGCCC TCAGCAGTTT CTAGTGAATC
ATCAGATGTT TCCAGGGTGC CCCAAGGACC TGAAAATGAC CCTGTACCTT ATTTGAACTA
ACCAATCAGT TCGCTTCTCG CTTCTGTTCG CGCGCTTCCG CTCTCCGAGC TCAATAAAAG
AGCCCACAAC CCCTCACTCG GCGCGCCAGT CTTCCGATAG ACTGCGTCGC CCGGGTACCC
GTATTCCCAA TAAAGCCTCT TGCTGTTTGC ATCCGAATCG TGGTCTCGCT GTTCCTTGGG
AGGGTCTCCT CTGAGTGATT GACTACCCAC GACGGGGGTC TTTCATTTGG GGGCTCGTCC
GGGATTTGGA GACCCCTGCC CAGGGACCAC CGACCCACCA CCGGGAGGTA AGCTGGCCAG
CAACTTATCT GTGTCTGTCC GATTGTCTAG TGTCTATGTT CCGGGACCCG CGCCTGCGTC
TGTACTAGTT AGCTAACTAG CTCTGTATCT GGCGGACCCG TGGTGGAACT GACGAGTTCT
GAACACCCGG CCGCAACCCT GGGAGACGTC CCAGGGACTT TGGGGGCCGT TTTTGTGGCC
CGACCTGAGG AAGGGAGTCG ATGTGGAATC CGACCCCGTC AGGATATGTG GTTCTGGTAG
GAGACGAGAA CCTAAAACAG TTCCCGCCCT CGTCTGAATT TTTGCTTTCG GTTTGGAACC
GAAGCCGCGC GTCTTGTCTG CTG
```

ψ+
```
CAGCATCGTT CTGTGTTGTC TCTGTCTGAC TGTGT
TTCTGTATTT GTCTGAAAAT TAGGGCCAGA CTGTTACCAC TCCCTTAAGT TTGACCTTAG
GTCACTGGAA AGATGTCGAG CGGATCGCTC ACAACCAGTC GGTAGATGTC AAGAAGAGAC
```

FIGURE 8B

```
GTTGGGTTAC CTTCTGCTCT GCAGAATGGC CAACCTTTAA CGTCGGATGG CCGCGAGACG
GCACCTTTAA CCGAGACCTC ATCACCCAGG TTAAGATCAA GGTCTTTTCA CCTGGCCCGC
ATGGACACCC AGACCAGGTC CCCTACATCG TGACCTGGGA AGCCTTGCT TTTGACCCCC
CTCCCTGGGT CAAGCCCTTT GTACACCCTA AGCCCTCCGCC TCCTCTTCCT CCATCCGCCC
CGTCTCTCCC CCTTGAACCT CCTCGTTCGA CCCCGCCTCG ATCCCTCCCTT TATCCAGCCC
TCACTCCCTC TCTAGGCGCC GGAATT
```

HIS D

```
GATCCCCGGAC CATGAGCTTC AATACCCTGA TTG
ACTGGAACAG CTGTAGCCCT GAACAGCAGC GTGCGCTGCT GACGCGTCCG GCGATTCCG
CCTCTGACAG TATTACCCCG ACGGTCAGCG ATATTCTGGA TAATGTAAAA ACGGCGGGTG
ACGATGCCCT GCGTGAATAC AGCGCTAAAT TTGATAAAAC AGAAGTGACA GCGCTACGCG
TCACCCCTGA AGAGATCGCC GCCGCCGGCG CGCGTCTGAG CGACGAATTA AAACAGGCGA
TGACCGCTGC CGTCAAAAAT ATTGAAACGT TCCATTCCGC GCAGACGCTA CCGCCTGTAG
ATGTGGAAAC CCAGCCAGGC GTGCGTTGCC AGCAGGTTAC GCGTCCCGTC TCGTCTGTCG
GTCTGTATAT TCCCGGCGGC TCGGCTCCGC TCTTCTCAAC GGTGCTGATG CTGGCGACGC
CGGCGCGCAT TGCGGGGATGC CAGAAGGTGG TTCTGTGCTC GCCGCCGCCC ATCGCTGATG
AAATCCCTCTA TGCCGGCGCAA CTTTAACGTC GGGCCGCGC
AGGCGATTGC CGCTCTGGCC TTCGGCAGCG AGTCCGTACC GAAAGTGGAT AAAATTTTG
GCCCCGGCAA CGCCTTTGTA ACCGAAGCCA CAGTCCAGGT CAGCCAGCGT CTCGACGGCG
CGGCTATCGA TATGCCAGCC GGGCCGTCTG AAGTACTGGT GATCGCAGAC AGCGGCGCAA
CACCGGATTT CGTCGCTTCT GACCTGCTCT CCCAGGCTGA GCACGGCCCG GATTCCCAGG
TGATCCTGCT GACGCCTGAT GCTGACATTG CCCGCAAGGT GGCGGAGGCG GTAGAACGTC
AACTGGGCGGA ACTGCCGCGC GCGGACACCG CCCGGCAGGC CCTGAGCGCC AGTCGTCTGA
TTGTGACCAA AGATTAGCG CAGTGCCGTCG CCATCTCTAA TCAGTATGGG CCGGAACACT
TAATCATCCA GACGCGCAAT GCGCGCGATT TGGTGGATGC GATTACCAGC GCAGGCTCGG
TATTTCTCGG CGACTGGTCG CCGGTGATTA CGCTTCCGGA ACCAACCATG
```

FIGURE 8C

TTTTACCGAC CTATGGCTAT ACTGCTACCT GTTCCAGCCT TGGGTTAGCG GATTTCCAGA
AACGGATGAC CGTTCAGGAA CTGTCGAAAG CGGGCTTTTC CGCTCTGGCA TCAACCATTG
AAACATTGGC GGCGGCAGAA CGTCTGACCG CCCATAAAAA TGCCGTGACC CTGCGCGTAA
ACGCCCTCAA GGAGCAAGCA TGAGCACTGA AAACACTCTC AGCGTCGCCG GGATC

AATTCGTTAA CTCGAGGATC
NSA MYO D

GGCCCAGCC ACCAGGATGG TATAGTATAG NATAGATTTT ATTTAGAGCA TAGGGAGGGG
AGTCAAGAGG GCAGTAGAGG CAAAGAAAGG AAGAGAGAGG GGGAGAGAAG AGAAGTAGAG
GTGTAGAGGC TGGCCTTGGA GCACGTGGAG AGAGCAGGGN AAAGGAATGG GGAGAGAGGG
NAGAATTGGA AACAGAGAAA GAGCAAGAGA GGATCAAGAG AGCAAGGAGG GGGGCAAGCA
GCCCNTTTTA TAGTGAGTCA GGCACACCTG GTTGTTGCCA GGTAACTGTG GGGCGGGGNT
TAGACACAAA GCTAAAAACA TCCACCACCT AGTTNATCTG CCAGACTCTC AAGTCCTCG
CATACCAGAG CCTGGGGGAA TCCCAGAGGG AGACATGTGA AGGCTCCCTG GGACCCTGGT
CAGGACNGGA CCATGTCTGT GCCCAGCCNG AGTTCCCTA AGGTCAGCCTA AATTGGCCAG
ATCTACACTT GGTGGCAGGC AGTTTCAGGC TTTCTGGGAA GCAAAACTGG CAGAGAACAG
AGCAGGATCC TTGAGTTGGG AAAGGAAAGT CTAGGGCCAG AGACTGAACC TGGGCTGGT
CCTGTTCCAC CTGTNCTCCC NGTGGTTTCA TCCTCCAGTC CTTCAGCCCC CTAGACCCAA
GCCAGCCATG CAGCCCGCAG TAGCAAAGTA AGAGGCCACA GGTCCAGACT GGGTAGGGCA
GAGGTGCCTG AGGCTTGGGG CAGGTGCTAG TTGGATCCGG TTTCCAGAGG CAATATATAT
ATAAAGGCTG CTGTTTCCCC GATGGTGCAA CACCCCAGAG GCCTAGCCAG ACCAACATTC
CTGCCNAAAA GCCAGCTCTC CATTTATAGC ACCTTGGAAG ACTAGCCAAG GGAGCTGAAA
TGCCAAGGCT GGAAAGGACA GGGGAAATC AAAGGCCAC CTATGGCGGC AGGAGAACTG
AGCCTCAGGA TGAGCTGTGT GCTTCTCCAG GTCAGTGGGC CTACAGCCTA AGAGGCCCTG
CATTGAGGGG ACAATGCCTC AGCCCAGAGC CAATGGCACG CTCCAGAAGG GGTGGCTGGG
GGAAGTTTTA GTGACCATAA AATAAAAAGC AAGGTTGCAA TCACTTAGAC TCAGCATAAA

FIGURE 8D
ATTTATTTCG GTTTTTNTAA ATTATTCGTT TTGTTATTTG TGTGCTTGCT TTGCTTTGCT
TTGTTTGCTC GGNGTAGACA CTGGAGAGGC TTGGGCAGGC TGCACCAGAT AGCCAAGTGC
TACCGCGTAT GGCTGCCAGT CTCTCTGCCC TCCTTCCTAG CTAGGCAGCT GCCCCAGCAC
AGAGTCGCGG GAGGGGGCAC TCCCTGGCCC CAGTGGCTAC CCTGGGGACC CCAAGCTCCG
CCCTACTACA CTCCTATTGG CTTGAGGCGG GGCTTTTAGG CTACCCCTGA TAAATAGCCC
AG

AGCTT
NEO
GGGCTGCAGG TCGAGGCGGA TCT
GATCAAGAGA CAGGATGAGG ATCGTTTCGC ATGATTGAAC AAGATGGATT GCACGCAGGT
TCTCCGGCCG CTTGGGTGGA GAGGCTATTC GGCTATGACT GGGCACAACA GACAATCGGC
TGCTCTGATG CCGCCGTGTT CCGGCTGTCA GCGCAGGGGC GCCCGGTTCT TTTTGTCAAG
ACCGACCTGT CCGGTGCCCT GAATGAACTG CAGGACGAGG CAGCGCGGCT ATCGTGGCTG
GCCACGACGG GCGTTCCTTG CGCAGCTGTG CTCGACGTTG TCACTGAAGC GGGAAGGGAC
TGGCTGCTAT TGGGCGAAGT GCCGGGGCAG GATCTCCTGT CATCTCACCT TGCTCCTGCC
GAGAAAGTAT CCATCATGGC TGATGCAATG CGGCGGCTGC ATACGCTTGA TCCGGCTACC
TGCCCATTCG ACCACCAAGC GAAACATCGC CGGCGGCTGC ATACGCTTGA TCCGGCTACC
TGCCCATTCG ACCACCAAGC GAAACATCGC ATCGAGCGAG CACGTACTCG GATGGAAGCC
GGTCTTGTCG ATCAGGATGA TCTGGACGAA GAGCATCAGG GGCTCGCGCC AGCCGAACTG
TTCGCCAGGC TCAAGGCGCG CATGCCCGAC GGCGAGGATC TCGTCGTGAC CCATGGCGAT
GCCTGCTTGC CGAATATCAT GGTGGAAAAT GGCCGCTTTT CTGGATTCAT CGACTGTGGC
CGGCTGGGTG TGGCGGACCG CTATCAGGAC ATAGCGTTGG CTACCCGTGA TATTGCTGAA
GAGCTTGGCG GCGAATGGGC TGACCGCTTC CTCGTGCTTT ACGGTATCGC CGCTCCCGAT
TCGCAGCGCA TCGCCTTCTA TCGCCTTCTT GACGAGTTCT TCTGAGCGGG ACTCTGGGGT
TC

FIGURE 8E

LTR

```
GATAAAATAA AAGATTTTAT TTAGTCT
CCAGAAAAAG GGGGGAATGA AAGACCCCAC CTGTAGGTTT GGCAAGCTAGCTTAAGTAAC
GCCATTTTGC AAGGCATGGA AAAATACATA ACTGAGAATA GAGAAGTTCAGATCAAGGTC
AGGAACAGAT GGAACAGCTG AATATGGGCC AAACAGGATA TCTGTGGTAAGCAGTTCCTG
CCCCGGCTCA GGGCCAAGAA CAGATGGAAC AGCTGAATAT GGGCCAAACAGGATATCTGT
GGTAAGCAGT TCCTGCCCCG GCTCAGGGCC AAGAACAGAT GGTCCCCAGATGCGGTCCAG
CCCTCAGCAG TTTCTAGAGA ACCATCAGAT GTTTCCAGGG TGCCCCAAGGACCTGAAATG
ACCCTGTGCC TTATTTGAAC TAACCAATCA GAGCCCCACA GTTCGCTTCT CGCTTCTGTTCGCGGCTTC
TGCTCCCCGA GCTCAATAAA AGAGCCCCAC ACCCCTCACT CGGG
GCGCCAGTCC TCCGATTGAC TGAGTCGCCC GGGTACCCGT GTATCCAATAAACCCTCTTG
CAGTTGCATC CGACTTGTGG TCTCGCTGTT CCTTGGGAGG GTCTCCTCTGAGTGATTGAC
TACCCGTCAG CGGGGGTCTT TCATTTGGGG GCTCGTCCGG GATCGGGAGACCCCCTGCCCA
GGGACCACCG ACCCACCACC GGGAGGTAAG CTGG
``` pBR322

```
CTGCCCTCGCG CGTTTCGGTG ATGACGGTGA AAA
CCTCTGACAC ATGCAGCTCC CGGAGACGGT CACAGCTTGT CTGTAAGCGG
ATGCCGGGAG CAGACAAGCC CGTCAGGGCG CGTCAGCGGG TGTTGGCGGG
TGTCGGGGCG CAGCCATGAC CCAGTCACGT AGCGATAGCG GAGTGTATAC
TGGCTTAACT ATGCGGCATC AGAGCAGATT GTACTGAGAG TGCACCATAT
GCGGTGTGAA ATACCGCACA GATGCGTAAG GAGAAAATAC CGCATCAGGC
GCTCTTCCGC TTCCTCGCTC ACTGACTCGC TGCGCTCGGT CGTTCGGCTG
CGGCGAGCGG TATCAGCTCA CTCAAAGGC GGTAATACGG TTATCCACAGA
ATCAGGGGAT AACGCAGGAAAAGAACATGTGA GCAAAAGGCC AGCAAAAGG
CCAGGAACCG TAAAAAGGCC GCGTTGCTGG CGTTTTTCCA TAGGCTCCGC
CCCCCTGACG AGCATCACAA AAATCGACGC TCAAGTCAGA GGTGGCGAAA
```

FIGURE 8F

```
CCCGACAGGA CTATAAAGAT ACCAGGCGTT TCCCCCTGGA AGCTCCCTCG
TGCGCTCTCC TGTTCCGACC CTGCCGCTTA CCGGATACCT GTCCGCCTTT
CTCCCTTCGG GAAGCGTGGC GCTTTCTCAT AGCTCACGCT GTAGGTATCT
CAGTTCGGTG TAGGTCGTTC GCTCCAAGCT GGGCTGTGTG CACGAACCCC
CCGTTCAGCC CGACCGCTGC GCCTTATCCG GTAACTATCG TCTTGAGTCC
AACCCGGTAA GACACGACTT ATCGCCACTG GCAGCAGCCA CTGGTAACAG
GATTAGCAGA GCGAGGTATG TAGGCGGTGC TACAGAGTTC TTGAAGTGGT
GGCCTAACTA CGGCTACACT AGAAGGACAG TATTTGGTAT CTGCGCTCTG
CTGAAGCCAG TTACCTTCGG AAAAAGAGTT GGTAGCTCTT GATCCGGCAA
ACAAACCACC GCTGGTAGCG GTGGTTTTTT TGTTTGCAAG CAGCAGATTA
CGGCGCAGAA AAAAGGATCT CAAGAAGATC CTTTGATCTT TTCTACGGGG
TCTGACGCTC AGTGGAACGA AAACTCACGT TAAGGGATTT TGGTCATGAG
ATTATCAAAA AGGATCTTCA CCTAGATCCT TTTAAATTAA AAATGAAGTT
TTAAATCAAT CTAAAGTATA TATGAGTAAA CTTGGTCTGA CAGTTACCAA
TGCTTAATCA GTGAGGCACC TATCTCAGCG ATCTGTCTAT TTCGTTCATC
CATAGTTGCC TGACTCCCCG TCGTGTAGAT AACTACGATA CGGGAGGGCT
TACCATCTGG CCCCAGTGCT GCAATGATAC CGCGAGACCC ACGCTCACCG
GCTCCAGATT TATCAGCAAT AAACCAGCCA GCCGGAAGGG CCGAGCGCAG
AAGTGGTCCT GCAACTTTAT CCGCCTCCAT CCAGTCTATT AATTGTTGCC
GGGAAGCTAG AGTAAGTAGT TCGCCAGTTA ATAGTTTGCG CAACGTTGTT
GCCATTGCTG CAGGCATCGT GGTGTCACGC TCGTCGTTTG GTATGGCTTC
ATTCAGCTCC GGTTCCCAAC GATCAAGGCG AGTTACATGA TCCCCCATGT
TGTGCAAAAA AGCGGTTAGC TCCTTCGGTC CTCCGATCGT TGTCAGAAGT
AAGTTGGCCG CAGTGTTATC ACTCATGGTT ATGGCAGCAC TGCATAATTC
TCTTACTGTC ATGCCATCCG TAAGATGCTT TTCTGTGACT GGTGAGTACT
CAACCAAGTC ATTCTGAGAA TAGTGTATGC GGCGACCGAG TTGCTCTTGC
```

FIGURE 8G

```
CCGGCGTCAA CACGGGATAA TACCGCGCCA CATAGCAGAA CTTTAAAAGT
GCTCATCATT GGAAAACGTT CTTCGGGGCG AAAACTCTCA AGGATCTTAC
CGCTGTTGAG ATCCAGTTCG ATGTAACCCA CTCGTGCACC CAACTGATCT
TCAGCATCTT TTACTTTCAC CAGCGTTTCT GGGTGAGCAA AAACAGGAAG
GCAAAATGCC GCAAAAAAGG GAATAAGGGC GACACGGAAA TGTTGAATAC
TCATACTCTT CCTTTTTCAA TATTATTGAA GCATTTATCA GGGTTATTGT
CTCATGAGCG GATACATATT TGAATGTATT TAGAAAAATA AACAAATAGG
GGTTCCGCGC ACATTTCCCC GAAAAGTGCC ACCTGACGTC TAAGAAACCA
TTATTATCAT GACATTAACC TATAAAAATA GGCGTATCAC GAGGCCCTTT
CGTCTTCAA
```

LHDMDN

MYOD REGULATORY REGION

This invention was made with government support under grants HL41212 and NS01108 awarded by the National Institutes of Health. The government has certain rights in the invention.

FIELD OF THE INVENTION

The invention relates to genetic engineering involving recombinant DNA technology, and particularly to expression vectors for tissue-specific transcription of genes in muscle cells.

BACKGROUND OF THE INVENTION

The myoD gene converts many differentiated cell types into muscle cells. MyoD protein is a member of the basic-helix-loop-helix (bHLH) family of proteins; this 68-amino acid domain in MyoD is necessary and sufficient for myogenesis. The MyoD protein is sufficient to orchestrate the coordinated expression of most, if not all, of the skeletal myogenic program in cell types derived from all three germ layers of the embryo. As such, the regulation of Myo D expression and protein activity creates a nodal point, or master switch, that integrates the genetic and environmental influences on a cell. The expression and activity of the MyoD protein is regulated, in part, by interactions with members of a large family of proteins related to MyoD by sequence homology, the helix-loop-helix (HLH) proteins. MyoD binds cooperatively to muscle-specific enhancers and activates transcription. The helix-loop-helix (HLH) motif is responsible for dimerization, and, depending upon its dimerization partner, MyoD activity can be controlled.

MyoD is a nuclear protein, 318 amino acids in length, that binds to many muscle-specific enhancers. Although it is phosphorylated, the function of the phosphorylation has not been defined. The protein and RNA turn over rapidly. MyoD binds to a consensus DNA binding sequence that includes a CAN NTG sequence (N represents A, T, G, or C) present in most muscle-specific enhancers (1; see the appended Citations).

MyoD Family

To date, four different, but related, genes have been reportedly cloned from muscle cells: myoD, encoding the MyoD protein; myogenin; myf-5; and the gene encoding MRF4/Herculin/Myf6 (2–8). Each is sufficient to activate the myogenic program when expressed in a non-muscle cell line, and together they encode the MyoD family of myogenic regulatory proteins.

MyoD alone is sufficient to activate the myogenic program without the a priori cooperation of other muscle-specific factors. Myogenic regulatory genes are capable of interacting with and suppressing tissue-specific regulatory factors in other cell types, such as fibroblasts, even when those cells would not ordinarily express myogenic genes. The MyoD protein seems to activate myogenesis by directly binding to the control regions of muscle-specific genes (1).

In in vitro gel shift assays MyoD protein binds DNA and paired MyoD protein binding sites are reportedly essential parts of several characterized enhancers of muscle-specific genes (1, 9–11). MyoD reportedly binds cooperatively to the paired sites in the muscle creatine kinase (MCK) enhancer, and deletion analysis suggests that the $NH_2$-terminal 50 amino acids are necessary for this cooperativity (9). In enhancers that contain two MyoD protein binding sites apparently both are necessary for full enhancer activity, arguing for the functional importance of cooperative binding. In contrast, some enhancers, such as that for alpha-cardiac actin, contain a single identified MyoD binding site (12). In this case the adjacent CArG and SP1 binding sites can repotedly functionally substitute for the second MyoD binding site (12), because the enhancer activity is dependent on the presence of all three sites.

In vitro DNA binding assays suggest that heterodimerization of the MyoD family of myogenic bHLH proteins with an E2A protein may be crucial for functional activity. MyoD and related myogenic bHLH proteins have a relatively weak binding affinity to the CANNTG sites in the MCK enhancer, whereas the heterodimer formed with an E2A protein binds with much higher affinity (13–15). That is, MyoD can bind DNA as a homodimer, but it binds to its target sequence more than ten times better (16) as a heterodimer with one of the bHLH proteins encoded by the E2A gene, first identified by Murre et al. (15). The E2A gene product is ubiquitously expressed and encodes Coy differential splicing), for at least three different bHLH proteins, E12, EA7, and ITF1 (25,26). Analysis of the binding site preferences for MyoD and E2A proteins show that each has a slightly different preferred half-site, giving homodimers and heterodimers slightly different preferred binding sequences (18). Mutations of the MyoD basic region, when compared to wild-type MyoD, show that some mutants bind with similar or better affinity to the MyoD binding sites in the MCK enhancer but do not activate transcription (15), arguing that the $NH_2$-activation domain of MyoD is usually "hidden" from the transcriptional machinery and that activation of the region can be regulated independent of DNA binding. Methylation interference indicates that the basic region of the bHLH proteins interacts with the major groove of the DNA double helix (1). In order to activate muscle-specific genes, MyoD protein complexes must bind to two or more upstream sites (9,13,16). As assayed by dissociation rate, MyoD binds cooperatively, mediated by its $NH_2$-terminal acidic domain, which also harbors the activation function.

Domain-swapping experiments with achaete-scute showed that the helix 1, loop, or helix 2 regions could be exchanged into MyoD without loss in the ability of the chimeric MyoD to form dimers with E2A, to bind to muscle-specific enhancers, or to activate myogenesis in C3H 10T1/2 cells. However, swapping of the basic region of achaete-scute into MyoD resulted in chimeric protein that could bind specifically to muscle-specific enhancer DNA and dimerize with E2A, but it failed to induce muscle-specific differentiation or trans-activation of muscle-specific reporter genes. The same result occurs when the E2A basic region is swapped into MyoD, and in this case the E2A basic region differs from MyoD in only four of ten positions which are conserved among the MyoD family. Changing just one of these E2A residues back to the corresponding MyoD amino acid (an alanine) restores DNA binding, but myogenic activity still fails to occur. Changing the second amino acid, back to a threonine, restores myogenic activation (19). These results show that the specificity for myogenic activation resides in the basic region of MyoD and have led to the suggestion that activation requires properties of both the DNA sequence and the basic region of the MyoD protein.

Control of MyoD protein

Negative and positive (20) mechanisms for regulating MyoD have been postulated. One possible mechanism of negatively regulating the activity of the myogenic bHLH proteins such as MyoD is by decreasing the available pool of E2A proteins through dimerization with the HLH protein Id (21). This protein shares the HLH domain but lacks an adjacent basic region, thereby rendering it incapable of binding DNA, but capable of binding other HLH proteins. It has been demonstrated in vitro that Id dimerizes with the E2A protein products with a relatively high affinity. That is, Id binds about five-fold better to E2A than to MyoD, and when added to MyoD-E2A-DNA complexes at 37° C. Id rapidly causes dissociation of the complexes. Thus, by competing for HLH dimerization regions Id can prevent the formation of MyoD:E2A protein oligomers. Because Id lacks a region equivalent to the DNA binding domain of the bHLH proteins, Id-containing hetero-oligomers do not bind to core CANNTG sequence. For protein complexes containing Id, the choice is probably on-or-off; for complexes of E2A or MyoD homodimers or heterodimers, the results can be altered DNA binding specificity. In many cell lineages, including muscle, when the cells are induced to differentiate the level of Id mRNA declines (21). MyoD expression also decreases when cells are transformed with transforming agents (22, and citations therein).

Regulation of the myoD gene

MyoD protein is expressed only in skeletal muscle. Cardiac and smooth muscle, which express many of the same muscle-specific structural genes as skeletal muscle, reportedly do not express MyoD protein (2,23). Factors that influence growth regulate expression of MyoD protein, but MyoD protein itself can also inhibit cell growth (24). MyoD protein inhibits the cell cycle directly (24). MyoD protein is capable of positively regulating its own expression, and "autoactivation" mechanisms have also been postulated. The nucleotide sequence of the regulatory regions of the MyoD gene has not been identified, until now.

MyoD transfection of cells

Transfection of LTR-myoD constructs into non-muscle cells can inhibit cell growth (24). MyoD inhibits the cell cycle directly and when introduced into cells prevents entry of the cells into S phase (24). The myoD gene is capable of activating previously silent muscle-specific genes when introduced into a variety of differentiated cell types with a viral long terminal repeat (LTR) used to promote constitutive transcription (2,25,26,29). Because MyoD molecules with mutations in the basic (DNA binding) region still cause growth arrest, it would seem that MyoD protein can halt the cell cycle independent of its ability to induce myogenesis. In certain cell types, the entire program for muscle differentiation seems to be activated (26). The range of cell types converted to muscle by the myoD gene includes a number of fibroblast cell lines, adipocytes, melanoma cells, a hepatoma cell line, neuroblastoma cells, osteosarcoma cells, and P19 teratocarcinoma cells, as well as primary cultures of chondrocytes, smooth muscle, retinal pigment, fibroblasts, and brain cells. In primary fibroblasts, MyoD expression is repressed by transacting factors (27), and during development myoD transcription may require, among other things, the removal of negative control.

Cotransfection of a MyoD expression vector with a muscle-specific expression vector carrying a single MyoD binding site results in no activity. Cotransfection with a vector carrying two sites lead to high levels of activity; however, if a third plasmid carrying a single site is also included and is in excess, inhibition occurs. This suggests that plasmids carrying a single site will compete specifically for the activation of a vector with two sites. This suggests (as noted above) that binding to a single DNA site is not sufficient to accomplish transcriptional activation of a muscle-specific gene and that, like other activator proteins (28), MyoD must occupy two or more sites before transcription is initiated.

The apparent simplicity of the observed MyoD myogenic effect in transfected cells belies a rather sophisticated interplay between the cooperative interactions of at least MyoD, E2A, and Id proteins, the multiple DNA regulatory sites that bind these factors, and cell type-specific and differentiation-specific transcriptional activation factors in cells that bind at other regulatory sites. The varied and complex effects of oncogenes, anti-oncogenes, and growth factors on MyoD expression and activity may also contribute to the failure of some cells to activate myogenic genes after introduction of MyoD (25).

Despite numerous attempts to identify the regulatory regions controlling expression of MyoD, these sequences have remained elusive. Without delineation of the myoD regulatory regions and definition of their specific interactions with MyoD, it has not been possible to engineer a vector that will reproduce the endogenous natural control of MyoD expression in a cell, or to select for cells expressing MyoD, or to utilize the myoD regulatory region to control other genes of interest in a tissue-specific manner in skeletal muscle cells or precursors to those cells. It would be highly desirable to have a source of isolated DNA capable of faithfully reproducing the natural mechanisms of regulation of MyoD expression in a cell, because MyoD expression would be useful for engineering transplantable skeletal muscle cells, or for targeting gene expression in a tissue-specific manner to skeletal muscle.

SUMMARY OF INVENTION

The invention provides nucleotide sequences of the myoD regulatory region containing both proximal promoter and distal enhancer regulatory regions and their constituent regulatory elements. The myoD regulatory region alone is sufficient to faithfully reproduce the natural mechanisms of regulation of MyoD expression in a cell. It is now possible to select for MyoD-expressing cells, e.g., by using a selectable marker regulated by the myoD regulatory region. By selecting MyoD expressing cells it is now possible to genetically engineer pre-muscle cells that can be selected and substantially purified for transplantation. Aspects of the invention also provide the regulatory region of the myoD gene for controlling other genes of interest in a tissue-specific manner in both myoblasts and early myotubes.

BRIEF DESCRIPTION OF THE DRAWINGS

FIGS. 1A, 1B, and 1C together show the nucleotide sequence of the proximal regulatory region (PRR) of the myoD gene (SEQ ID NO:1);

FIG. 4A and 4B together show the nucleotide sequence of the distal regulatory region (DRR) of the myroD gene;

FIGS. 7A, 7B, 7C, 7D, 7E, 7F, and 7G together show SEQ ID NO:3, comprising the LTR, Ψ, HisD, neo, and pBR322 regions of the myoD retroviral expression vector pLHDMDN.531;

FIGS. 8A, 8B, 8C, 8D, 8E, 8F, and 8G together show SEQ ID NO:4, comprising the LTR, Ψ, HisD regulatory, neo, and pBR322 regions of the myoD retroviral expression vector pLHDMDN.NSA.

DETAILED DESCRIPTION OF THE PREFERRED EMBODIMENT

Figure 2:
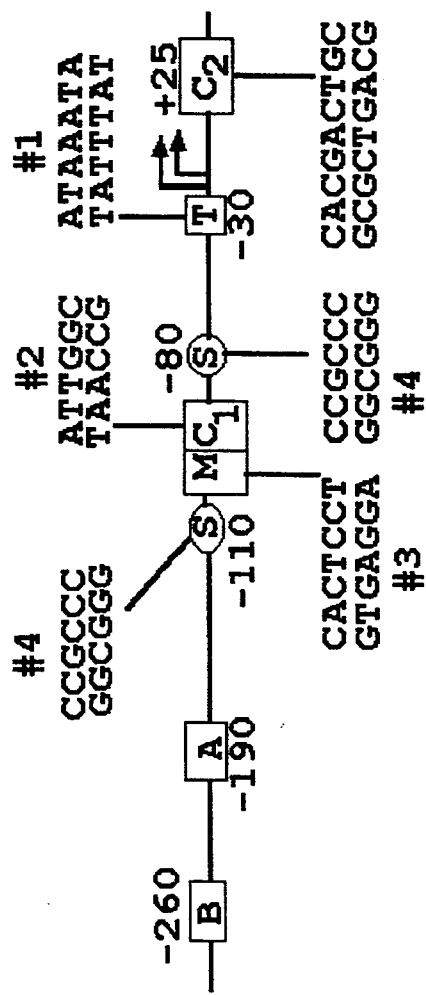
FIG. 2 schematically depicts the organization of the proximal regulatory region (PRR) of the myoD gene.

Initial attempts to identify the activity of the myoD regulatory region by transient transfection of conspecific mouse cells were unsuccessful. However, surprisingly, chicken myocytes were responsive to mouse myoD proximally regulatory region constructs containing promoter elements in transient transfection assays, and initial characterization of proximal regulatory regions was accomplished using these cells. In experiments to determine why transfection of mouse myoD regulatory regions in mouse cells were nonfunctional, the location of the upstream distal enhancer regulatory region of the myoD gene was identified. It was discovered that the failure to earlier demonstrate these distal enhancer regions was due to their inability to function in cells unless they are integrated in a stable manner into the genome of the recipient cell.

The identification of the proximal and distal regulatory regions provides sequences that normally control the tissue-specific expression of MyoD in muscle cells, and thereby myogenesis. The specific DNA regulatory sites of myoD were identified in the 5' flanking sequences of the myoD gene in a region from −7000 to +140 relative to the major transcriptional start of the cDNA.

A plasmid vector (pKCAT2) containing the 7 kb myoD genomic 5' regulatory region has been deposited with the American Type Culture Collection (ATCC), Rockville, Md., and granted accession No. 75091.

Retrovital vector "LHDMDN.531" containing 2,244 bp of myoD genomic 5' regulatory region (i.e., including both the PRR and DRR regions, below) has been deposited with the ATCC, and has been granted Accession No. 75092.

The following terms as used herein are intended to mean the following:

"MyoD regulatory region" as used herein describes a region of 5' myoD genomic DNA nucleotide sequence from −7000 to +140 relative to the major transcriptional start of the cDNA and inclusive of the PRR and DRR.

"PRR" is used to mean the myoD proximal regulatory region shown from positions 1 to 1620 in FIG. 1A, and inclusive of the regulatory elements from positions 590 to 900 in FIG. 1A.

"DRR" the used to mean the myoD distal regulatory regions shown from positions 1 to 1200 in FIG. 4A, and inclusive of the regulatory elements from positions 421 to 1200 in FIG. 4A.

"Capable of hybridizing under stringent conditions" means annealing to one of the myoD regulatory regions (shown in FIGS. 1A–C or 4A or 4B), or its complementary strand, under standard conditions, e.g., high temperature and/or low salt content which tend to disfavor hybridization. A suitable protocol (involving 0.1×SSC, 68° C. for 2 hours) is described in Maniatis, T., et al., Molecular Cloning: A Laboratory Manual, Cold Spring Harbor Laboratory, 1982, at pages 387–389.

"bHLH" means polypeptides having the helix-loop-helix motif and a basic DNA binding region as described in the Background section, above.

"bHLH dimer binding site" means a myoD regulatory region nucleic acid capable of binding a bHLH oligomer consisting of two or more bHLH polypeptides in a complex, and wherein the complex is capable of binding to the bHLH dimer binding site in the nucleic acid. Representative examples of bHLH genes include, but are not limited to, myoD, myogenin, myf-5, and the gene encoding MRF4/Herculin/Myf6. Representative bHLH dimer binding sites include, but are not limited to, MyoD binding sequences (e.g., CANNTG), and also, including the bHLH dimer binding sites in PRR at positions 595 to 606, positions 666 to 675, and positions 875 to 883 shown in FIG. 1A; and, in the DRR, at positions 265 to 270, positions 486 to 491, positions 608 to 613, and positions 741 to 746 shown in FIG. 4A.

"SP1 site" means a myoD regulatory region nucleic acid capable of binding a protein that binds to an SP1 site having a nucleotide sequence with GGGCGG. Representative SP1 binding sites include, but are not limited to, sites in PRR at positions 740 to 745 shown in FIG. 1A; and, in DRR, at positions 291 to 297 shown in FIG. 4A.

"M-CAT site" means myoD regulatory region nucleic acid capable of binding a protein that binds to an M-CAT site having a nucleotide sequence with CATTCCT. Representative M-CAT binding sites include, but are not limited to, sites in PRR at positions 751 to 757 shown in FIG. 1A; and, in DRR, at positions 163 to 169 shown in FIG. 4A.

"CAAT box" means a myoD regulatory region sequence motif, such as CAAT box sequences (e.g., AACCAAT and GGCCAAT) that are often incorporated into a "CArG box" in other muscle promoters. The "CArG box" means a CC(A/T)$_6$GG sequence that binds SRF and other factors. In myoD the CAAT box is part of a CC(A/T)$_4$GG motif, that is similar to the CArG box motif. A representative example of a CAAT box sequence in the myoD regulatory region is found in the PRR at positions 758 to 763 shown in FIG. 1A; and a representative example of a CArG box is found in the DRR at positions 467 to 476 shown in FIG. 4A.

"ATAAATA region" means a myoD regulatory region sequence capable of hybridizing under stringent conditions to the sequence at positions 821 to 830 shown in FIG. 1A. "TATA element" and "TATA box" are also used interchangeably to refer to this element of the PRR.

"MEF binding site" means a myoD regulatory region nucleic acid capable of binding a protein that binds to an MEF site. Representative MEF binding sites include, but are not limited to, sites in the DRR at positions 312 to 321 and at positions 1097 to 1105 shown in FIG. 4A.

"AP1 binding site" means a myoD regulatory region nucleic acid capable of binding a protein that binds to an AP1 site. A representative AP1 binding site is found in the DRR at positions 254 to 260 shown in FIG. 4A.

"Operably-linked" is used to refer to linkage of a gene of interest to a myoD regulatory region nucleic acid such that the regulatory element(s) in the myoD regulatory region are capable of regulating downstream transcription of the gene of interest in a manner similar to the regulation of MyoD protein expression in skeletal muscle cells.

"Subtractive deletion" is used to mean the process of removing portions of nucleic acid sequence from a DNA or RNA, and subsequently testing the functional activity of the deleted sequence, so that regions exerting regulatory control or regions contributing to functional activity of a protein are identified.

The invention provides DNA or RNA expression vectors containing a myoD regulatory region for introducing a gene of interest into a cell, such that the gene of interest is regulated in a tissue-specific manner in muscle cells. Useful vectors for these purposes include infectious DNA and RNA vectors. Representative vectors include retroviral, vaccinia, adenovirus, CMV vectors, and other such genetically engineered viral vectors, as well as plasmid vectors useful in transfecting cells. The expression vectors are constructed with a myoD regulatory region operably linked to a gene of interest, and transcription of the gene of interest is controlled by the MyoD regulatory region when the vector is introduced into the cell. When the vector DNA is integrated in the host-cell DNA, transcription of the vector DNA is regulated in a muscle-specific manner by the myoD regulatory region sequence(s). That expression of the gene of interest is so regulated, i.e., in a muscle-specific manner, can be determined by introducing the vector into muscle and non-muscle cells and observing the transcription or translation of the gene of interest in the muscle cell, such as by monitoring mRNA, protein, or protein functional activity, e.g., enzymatic activity or drug resistance. Useful muscle cells in which muscle-specific expression will occur include cells such as pre-muscle cells, myocytes, myoblasts, and also cells that have been genetically-engineered to incorporate at least one myoD gene into their genome so that they express MyoD protein. Cells transduced or transfected with expression vectors containing the myoD-regulatory-region are therapeutically and commercially useful, e.g., for (i) construction of tissue-specific gene transfer vectors; (ii) production of genetically-engineered proteins, i.e., by tissue-specific expression a gene of interest; (iii) muscle transplantation; (iv) expression of genes that regulate growth of myoblasts; and (v) expression of mutant forms of MyoD that modulate muscle differentiation. The expression vectors containing myoD regulatory region have the advantage that transcription of the gene of interest will occur in pre-muscle cells, myoblasts, and the like, but when the cells mature into myotubes (i.e., skeletal muscle) the expression of MyoD and the gene of interest will be down-regulated.

Positive selection using MyoD regulatory DNA and RNA

The invention provides myoD regulatory region DNA and RNA for expression of genes that encode marker proteins in replicating myoblasts and pre-muscle cells. Representative examples of marker proteins include marker enzymes (e.g., β-galactosidase, alkaline phosphatase, and the like), drug resistance markers (e.g., neomycin phosphotransferase, hygromycin, methotrexate, and the like), and antigenic and adhesion markers (e.g., such as can be sorted, panned, or identified by immunochemical or in vitro methods). These markers will be recognized as those elements conferring a phenotype that can be positively selected for, or a genotype that confers a selective growth advantage to the cells expressing the gene of interest, in this case either in vitro or in vivo. Positive selection of such myoblast and pre-muscle cells thus provides a way of obtaining substantially pure cell cultures of myoblasts, myocytes, pre-muscle cells, and the like. To be active the gene of interest is preferably operably linked to the myoD regulatory DNA or RNA so that the regulatory region elements exert effects on the gene of interest in a manner similar to those exerted on the myoD gene when it is residing in the genome of a muscle cell.

The invention also provides myoD-regulatory expression vectors for inducing a muscle phenotype in a non-muscle cell. In this case, the MyoD protein coding sequence and the myoD regulatory region are both introduced into the non-muscle cell, such that transcription of the myoD coding region is controlled by the myoD regulatory region. Expression of MyoD in turn activates muscle-specific genes in the cell and directs the cell to become a muscle cell. Fibroblasts are representative of a cell type that may be so induced to become a muscle cell.

Negative selection using myoD regulatory DNA and RNA

Rhabdomyosarcoma (RMS) tumors are tumors of skeletal muscle and represent one of the most common such solid tumors of childhood. All RMS are thought to express MyoD mRNA and protein, and, as such, MyoD expression is beginning to be used to classify solid tumors. While there have been real advances in the chemotherapeutic treatment of RMS tumors, a significant percentage remain refractory to chemotherapy. It is now possible, however, using myoD regulatory DNA and RNA in chimeric expression vectors to genetically alter RMS cells to broaden their sensitivity to chemotherapeutic agents. For example, such tumors can be genetically engineered to convert a prodrug to an active drug. A representative example is provided by genetically engineered tumor cells expressing a Herpes Simplex Virus thymidine kinase gene (HSV-tk). Such cells become sensitive to the prodrugs Gancyclovir and Acyclovir, i.e., guanosine analogs, because these prodrugs are substrates specific for the HSV-TK enzyme, and enzymatic conversion of the prodrug to an active drug takes place in these cells. Thus, the cytotoxicity of the drug, e.g., converted Gancyclovir and Acyclovir, is limited to cells expressing HSV-TK. While this general approach has been employed previously, there has been a general problem in targeting the expression of the HSV-tk gene in only tumor cells, and without such targeting significant toxicity could result. However, since expression of the myoD gene is restricted to skeletal muscle cells, and retroviral integration is restricted to replicating cells, the subject retroviral vectors, in which a gene of interest, in this case a therapeutic gene, is placed under the control of muscle-specific myoD regulatory DNA and RNA, will only be expressed in proliferating muscle cells and sarcoma cells. Representative examples of such therapeutic genes include genes encoding enzymes that convert pro-drugs to drugs, genes encoding toxins (e.g., ricin A chain and the like) and metabolic poisons, and genes encoding antiproliferative drugs. Thus, the provision of myoD regulatory DNA and RNA solves the problem of tissue-specific gene expression required for gene therapy in RMS cancer by targeting expression of the therapeutic gene to only tumor cells. Retroviral vectors are just one representative example of genetically engineered expression vectors that are useful in these therapeutic protocols.

The myoD PRR and DRR regulatory regions are useful as promoters and enhancers to regulate the expression of the HSV-tk gene, and other genes of interest. The results presented below demonstrate that myoD regulatory DNA and RNA can regulate expression of non-muscle genes, i.e., CAT, or neomycin drug resistance, in muscle cells transformed or transduced with expression vectors. The subject myoD regulatory DNA and RNA is useful in retroviral (and other) expression vectors for restricting expression of therapeutic genes to replicating skeletal muscle precursor cells and tumor cells in therapeutic protocols. Since the retroviral vector construct containing the myoD regulatory DNA and RNA will only express in replicating muscle cells and tumor cells, the other non-tumor cells of the host will be immune from the effects of the HSV-tk gene. In non-damaged muscle the fused myotubes and satellite cells are not replicating, and thus the predominant effects of the retroviral gene transfer will be limited to the tumor cells. This approach has particular merits for targeting tumor cells in RMS, e.g., for therapeutic intervention with Acyclovir and Gancyclovir as an adjunct to conventional chemotherapy. However, it is understood that genes other than HSV-tk and drugs other than Acyclovir or Gancyclovir will also be useful in similar protocols.

Enrichment for muscle cells in heterogeneous primary tissue cultures myoD regulatory DNA and RNA is also useful for enriching primary cell cultures to obtain substantially purified cultures of myoblasts. In this case, expression vectors are constructed wherein a marker gene (e.g., drug resistance or an enzymatic marker such as betagalactosidase) is placed under the regulatory control of the myoD regulatory DNA and RNA. When these vectors are introduced into myocytes (e.g., by transfection or transduction), and the cells are selected for the marker gene (e.g., drug resistance), only muscle cells, i.e., cells with endogenous or engineered MyoD protein expression, will be selected. This, method provides differential selection and elimination of cells unable to express the selectable gene, i.e., non-myoblast cells. This method of positive selection for muscle cells is especially useful in isolating and substantially purifying sources of genetically engineering cells, e.g., myoblasts, prior to transplantation.

Transplantation of allogeneic skeletal myoblasts shows promise already, without these selection methods, as an effective therapy for several neuromuscular degenerative disorders. However, success in the present therapeutic protocols often depends upon myoblasts expressing foreign histocompatibility antigens within a narrow range of limits, i.e., tissues with a good "match" of antigens between the donor and recipient. While it is fortunate that myoblasts express a relatively limited range of histocompatibility antigens, and are thus relatively weak immunogens, the cultures of cells which are transplanted are often heterogeneous and contain non-muscle cells (e.g., fibroblasts and tissue macrophages) that are highly immunogenic and capable of inducing an unfavorable immune response in the recipient, leading to elimination of the transplanted muscle cells. Currently, several techniques are used in an attempt to purify muscle cells for transplantation. These include growth of the heterogeneous cell cultures under selective growth conditions, panning techniques with specific substrates that favor attachment of muscle cells, and antibody-mediated panning or FAGS sorting. Antibody-mediated sorting methods have proven capable of providing purification relatively pure cultures of muscle cells; however, these techniques suffer from the additional disadvantage that the transplantable cells contain a foreign antibody on their cell surfaces. The foreign antibody may act both as an immunogen, i.e., inducing an immune response, and as an immune opsonic stimulant, i.e., stimulating an immune response to antigens of the skeletal muscle cell.

Selecting muscle cells based on the expression of marker genes under the control of the myoD regulatory region DNA and RNA offers significant advantages in efficiency and purity for muscle cell cultures useful in transplantation. Using positive selection methods is possible to substantially enrich populations of muscle cells that have a purity preferred for transplantation, i.e., contaminating immunogenic cells are removed and the resultant muscle populations have lower immunogenicity and thus improved survival in the recipient.

In such transplantation protocols the most desirable cell for use is the very early stage replicating myoblast. It is important, therefore, to use muscle promoter and enhancer regulatory sequences that are active as transcriptional control elements operative at an early stage in muscle differentiation. Muscle enhancer and promoter regions that have previously been described, i.e., from genes other than myoD, are not suitable for use because they direct expression of genes only in differentiated muscle cells. Thus, the subject myoD regulatory sequences offer the best regulatory elements for directing the expression of marker genes in these transplantable cell cultures that include such stages in muscle differentiation. The myoD regulatory sequence also offers the advantage that when the transplanted myoblasts have become established in the host, and differentiated into myotubes, MyoD expression is down-regulated. Thus, the invention offers the advantage of providing transient expression of a gene of interest in circumstances where this is desirable, or where it is desirable to have gene expression during development, (e.g., when treating developmental disorders, genetic diseases, and the like), or where it is desirable to have a gene that is actively expressed when muscle cells are proliferating and silent when they are not proliferating.

Conversion of non-muscle cells to muscle cells

Fibroblasts may actively suppress transcription of the myoD gene, and this may account for the lack of expression of this gene in some non-muscle cells. Deletional analysis, similar to that described below, in conjunction with transfection and transduction can identify the myoD negative regulatory region(s) responsible for suppression of MyoD expression in such non-muscle cells. These suppressor region nucleotide sequences can be separated from the myoD regulatory regions, or replaced by positively acting regulatory regions, and the cells convened from non-muscle cells to muscle cells.

Exuberant Production of Muscle

Agricultural uses are particularly contemplated for the myoD regulatory region. For example, expression of growth factor genes (e.g., encoding insulin, insulin-like growth factor, and the like) is useful when regulated by the myoD regulatory region for stimulating exuberant production of skeletal muscle in domestic animals. By using the myoD regulatory region to drive expression of such growth factors during the muscular development of a young animal, the number of muscle cells in the animal is increased relative to a non-treated animal. Since MyoD is normally down-regulated in myotubes, this intervention allows expression of the growth factor gene only during the developmental period, and leaves mature tissue free from the growth factor gene expression. As the increased number of myoblast mature into myotubes, a more rapid acquisition of muscle mass and/or larger muscle mass results than in untreated animals. This phenotypic result is commercially desirable in domestic animals, particularly in food animals such as beef and poultry.

Expression of gene in subsarcoplasmic domains of myotubes

Myotubes contain multiple nuclei, but it is known that some genes regulated by MyoD and Myogenin are expressed only in the nucleus that is under the synaptic cleft. The myoD regulatory region expression vectors pursuant to this disclosure can be used to determine which of the sub-synaptic nuclei in a myotube selectively express MyoD protein. Selective expression of MyoD by a nucleus allows the myoD regulatory regions vectors of this disclosure to be used for targeting gene expression, i.e., to a particular nucleus in a myotube (e.g., to provide a source of a protein of interest at a specific site within a myotube such as at a synaptic cleft).

Identification of nuclear factors binding the myoD regulatory region

The invention provides expression vectors useful for identifying nuclear regulatory proteins, e.g., transcription regulatory factors, that bind to the regulatory elements delineated in the proximal and distal portions of the disclosed myoD regulatory region. In a representative example of a positive selection method, myoD regulatory DNA or RNA is placed upstream from a marker gene, e.g., an enzyme such as $\beta$-galactosidase, and the construct is transfected or transduced into a series of mutant host cells, e.g., treated with a mutagenic agent causing DNA deletions, substitutions, or replacement. In this case, absence of expression of the marker gene in a host cell indicates the existence of a defective nuclear regulatory factor binding to the myoD regulatory region. Test assays and cell systems are thereby provided for cloning nuclear regulatory factors that influence the functional activity of the myoD regulatory region. In another example involving a negative selection method, a drug resistance marker gene is placed downstream from a myoD regulatory region. In this case, absence of expression of the marker gene in the host cell results in the death of the host cell, and by using replica plating techniques mutants that have altered nuclear regulatory factors influencing the disclosed myoD regulatory region are readily identified. Other representative assays useful for identifying nuclear factors binding myoD regulatory DNA is provided below in Example 4.

Identification of myoD regulatory regions in other species

It will be recognized by those skilled in the art that hybridization of nucleic acid with the disclosed mouse myoD regulatory region(s), or construction of test oligonucleotide probes based on the disclosed MyoD regulatory sequences, permissibility employing the test assays and schematic experimental approach of subtractive deletion and evaluation of marker gene expression and myogenesis outlined below in the Examples, provides the necessary information to readily identify corresponding MyoD regulatory regions in other animal species.

EXAMPLE 1

Isolation and Characterization of the myoD Gene

To isolate the myoD gene, a mouse liver cosmid library was screened with a MyoD cDNA. Seven cosmids were isolated that hybridized to the MyoD cDNA and restriction analysis demonstrated that these represented five distinct, overlapping cosmids that encompassed approximately 60 kb. The cDNA hybridization was limited to a region of about 3 kb. Sequence from this region confirmed the identity of the gene as myoD and demonstrated the presence of two introns (positions 1680 to 2125 and 2205 to 2523, FIGS. 1A–C), the first of which begins after the HLH domain. The sequence in FIG. 1A–C, entitled MYOD GENOMIC, also shows the nucleotide sequence from approximately position $-840$ (i.e., upstream from the major transcriptional start site) to position $+2790$. The genomic sequence is distinguished from the cDNA by showing three exons, two introns, and a short sequence of the 3' untranslated cDNA sequence (positions 3427 to 3443, FIG. 1C) that probably represents a divergence in the genomic sequence as a result of genetic polymorphism in this region between the C3H strain cells from which the cDNA was cloned and the A/J strain from which the genomic cosmid library was prepared, i.e., rather than a short intron.

RNAse protection assays on myoblast and myotube total RNA were used to determine the site of transcription initiation. The major fraction of the RNA extended approximately 40 nucleotides 5-prime of the previously characterized cDNA, and a minor fraction extended an additional 20 nucleotides 5-prime. These two putative transcription initiation sites were also obtained using primer extension assays. There was no apparent difference in the utilization of the two start sites in myoblasts or myotubes, nor was there a significant difference between azacytidine derived myoblasts and the C2 myoblast cell line.

C2 myoblast and myotube DNA were analyzed for hypersensitive sites using DNAse digestion. Sites were present in the promoter region and approximately 6 kb upstream of the start site. In addition, 3-prime of the start site, sites were present near the polyadenylation site and approximately 2 kb further 3-prime. No difference was noted between myotubes and myoblasts.

EXAMPLE 2

Identification and Characterization of Proximal Regulatory Regions (PRR)

Figure 5:
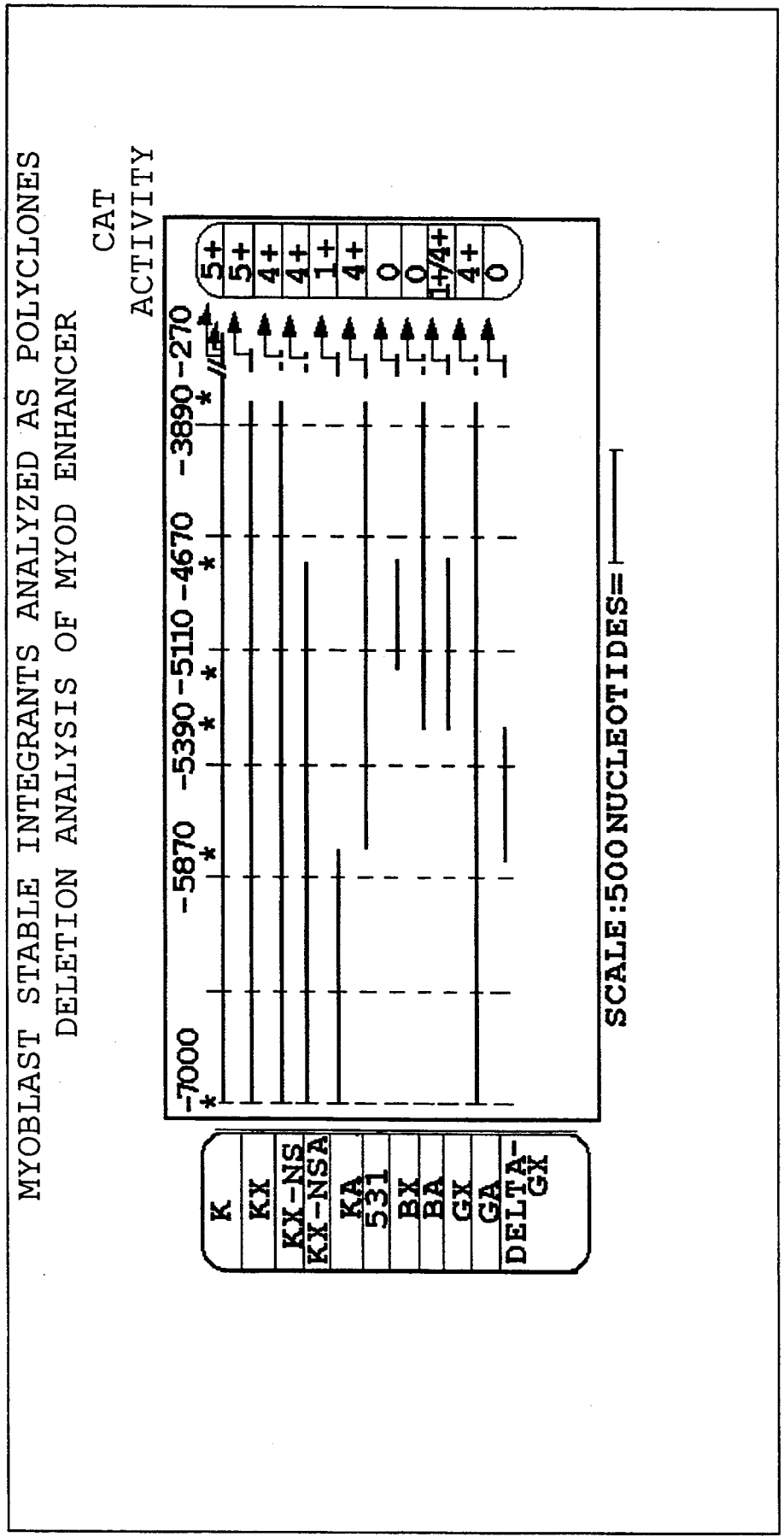
FIG. 5 schematically represents the deletion mutants constructed to identify the distal regulatory region (DRR) of the myoD gene.
Figure 6:
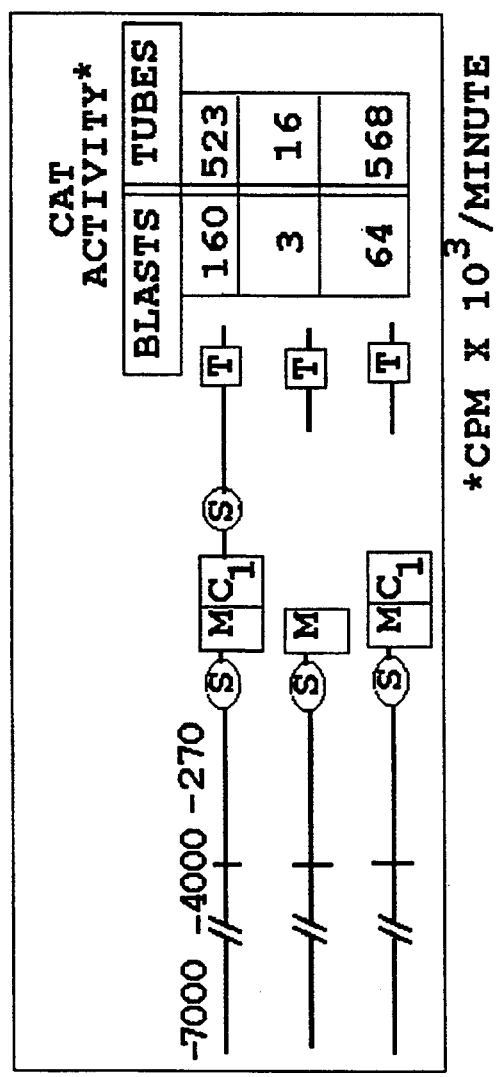
FIG. 6 presents data that shows the activity of myoD regulatory region in directing expression of a gene interest in a cell.
Figure 9:
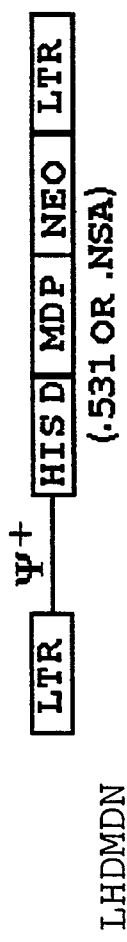
FIG. 9 shows schematiclaly the organization of the myoD retroviral expression vectors LHDMDN.531 and LHDMDN.NSA.

These studies identified a muscle-specific promoter region between positions 732 and 772 (as depicted in FIG. 1A) which together with the region between position 802 and 837 (FIG. 1A) was sufficient for induction of muscle-specific transcription. The regulatory region contains five interesting motifs: namely, 1. approximately 20 nucleotides upstream of the major start site is an AT-rich region similar to a TATA box, i.e., at positions 823 to 829, FIG. 1A, *1;
2. an inverted CAAT box, i.e., at positions 758 to 763, FIG. 1A, *2;
3. a near match of an M-CAT binding sequence, i.e., at positions 751 to 757, FIG. 1A, *3;
4. at least one SP1 site, i.e., at positions 740 to 745 as shown in FIG. 1A, 4, and 5. The MyoD binding sequence, i.e., at positions 677 to 682, FIG. 1A, the position of these sites in relation to the major start site for transcription is depicted in FIG. 2: namely, the inverted CAAT sequence ("C1"); a six-out-of-seven match to the M-CAT binding sequence ("M"); two potential SP1 binding sites ("S"); and the CANNTG core sequence ("A") creating a binding site for HLH proteins, including MyoD. A near direct repeat of a sequence surrounding the site at position −190 (FIG. 2, "A", nucleotides 666–675 of SEQ ID NO: 1) is found at position −260 (FIG. 2, "B", nucleotides 596–606 of SEQ ID NO: 1). Gel retardation assays using synthetic oligonucleotides demonstrated that the "A" site at −190 (FIG. 2) had a similar affinity for MyoD:E12 heterodimers as the MEF1 binding site (the "right" site) from the MCK enhancer. The "B" site at −260 (FIG. 2) also binds MyoD:E12 heterodimers, but with a lower affinity.

Portions of the myoD gene 5-prime to the point of translation initiation were cloned upstream of the bacterial reporter gene chloramphenicol acetyltransferase (CAT). These constructs were transfected into mouse muscle cell lines (both the C2 cell line and azacytidine derived myoblast lines) and into primary chick muscle cultures. Chimeric constructs were prepared using the regions upstream of the major transcriptional start site to drive the CAT reporter gene.

Figure 3:
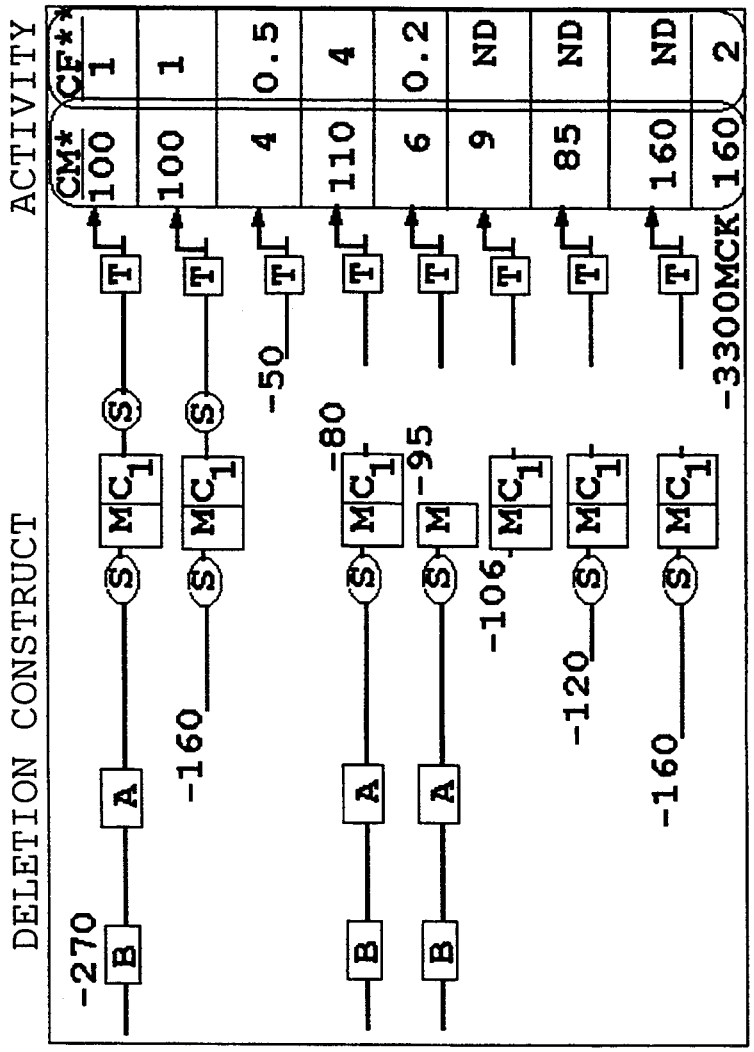
FIG. 3 schematically represents the deletion mutants constructed to identify the proximal regulatory region (PRR) of the myoD gene.

A deletion series of mutants was constructed (as depicted in FIG. 3) to study the functional activity of these upstream regions in mouse and chicken cells. (The "B", "A", "S", "M" and "C" sites are schematically depicted in FIG. 2, above.) In transient transfection assays using the complete upstream putative regulatory region of the myoD gene, mouse myocyte cell lines did not reliably demonstrate CAT activity above background levels. Surprisingly, and in distinct contrast, transient transfection of the regulatory region constructs into primary chicken myoblast cells did demonstrate high transcription activities in these cells (as determined by CAT activity). Studies of the deletion series of mutants in transient transfection of primary chick myocytes (CM) (using chick fibroblasts (CF) as a control) demonstrated the region between −270 and −50 conferred high levels of activity (FIG. 3, "CM"), whereas additional upstream sequence of up to 7 kb did not enhance this level of activity. (Note that the data presented in FIG. 3 for percentage expression of CAT in these cells have been normalized to 100%, relative to the −270 bp regulatory region construct and corrected for relative transfection efficiency.) This activity was specific to muscle cells in that the constructs were inactive in chick dermal fibroblasts. RNAse protection demonstrated that the constructs faithfully replicated the start sites of the endogenous gene in mouse muscle cells.

Additional deletions were made in the −270 bp regulatory region construct and these were again assayed for activity in primary chick muscle cultures and chick fibroblasts. Of interest is that the two MyoD binding sites (i.e., "A", "B", FIG. 2) can be deleted without any measurable loss of activity. In fact, a region of only 40 nucleotides in addition to the region of transcriptional initiation was both necessary and sufficient for nearly full activity as compared to the larger constructs. These 40 nucleotides contain the upstream SP1 site, i.e., "S" −110, FIG. 2, the CAAT box, i.e., "C1", FIG. 2, and the 6/7 match for the M-CAT sequence, i.e., "M", FIG. 2. Both the −110 SP1 site and the CAAT box were necessary for activity, since deletions disrupting either resulted in less than 10% wild-type activity.

EXAMPLE 3

Proximal Auto-Regulatory Region Regulation of MyoD Transcription

To investigate the possible functional significance of the region containing the MyoD binding sites, i.e., "A+ and "B", FIG. 2), the region between −260 and −90 was cloned upstream of the TK promoter driving a CAT reporter gene. Co-transfection of myoD constructs (or control constructs) with these CAT-reporter constructs into 10T1/2 fibroblasts with either MyoD demonstrated that MyoD led to a 5–10-fold trans-activation of the constructs containing the potential "A" and "B" MyoD binding sites (FIG. 2), supporting the notion that the binding sites may have a function in the auto-regulation of the myoD gene.

EXAMPLE 4

Tissue-Specific Factor(s) Interacting with Proximal Regulatory Region

Gel retardation assays were utilized to search for tissue-specific factors which might interact with the proximal regulatory region of myoD. Double strand synthetic oligonucleotides were used in the assays with nuclear extracts from cultured chick muscle or chick dermal fibroblasts.

An oligonucleotide containing the upstream SP1 site (−110 "S", FIG. 2) interacted with nuclear proteins in both dermal fibroblasts, skeletal muscle and skeletal muscle substituted with BrdU. In contrast, only skeletal muscle nuclear extracts contain a factor(s) that interacted with oligonucleotides containing the M-CAT ("M", FIG. 2) and CAAT ("C1", FIG. 2) sequences. Competition with an oligonucleotide containing a consensus M-CAT binding site, but no CAAT site, indicates that while some of the minor species of faster mobility may be specific to M-CAT binding factors, the predominant slow migrating species is not an M-CAT binding factor, and therefore is likely to be a CAAT binding protein(s). Of particular interest is the absence of the CAAT binding factor(s) in chick skeletal muscle substituted with BrdU. Together with the transient assays that show decreased activity of the proximal region constructs, the data are consistent with the notion that BrdU suppresses the expression or activity of a CAAT binding factor present in chick skeletal muscle that is necessary for the transcription of myoD. Thus, the combined results identify trans-acting transcription regulatory factors in chick skeletal muscle nuclear extracts that bind to at least the −110 SP1 site ("S", FIG. 2), the CAAT site ("C1", FIG. 2), the M-CAT site ("M", FIG. 2), and MyoD binding sites ("C2", "A", and "B", FIG. 2).

Nuclear extracts from the murine myoblast cell line C2C12 and the murine fibroblast cell line C3H10T1/2 (10T1/2) were also used in similar gel retardation assays. Both cell lines contained factors that interacted with the SP1 and CAAT containing oligonucleotides. The presence of the CAAT binding factor in the 10T1/2 cells may be relevant to the ability of this cell line to initiate MyoD expression either by treatment with the demethylating agent 5-azacytidine or by transfer of a myoD containing chromosome from a primary fibroblast.

EXAMPLE 5

Isolation of a Distal Regulatory Enhancer Region (DRR)

A distal regulatory enhancer region (DRR) was identified that confers myogenic activity in mouse myoblasts and myotubes. Since it is known that MyoD RNA and protein are expressed in replicating myoblasts as well as in myotubes, but in transient assays with mouse muscle myoblast lines we were unable to consistently demonstrate functional activity of our myoD-CAT reporter constructs in these cells (noted above), the possibility was investigated that other regulatory regions may exist. The regulatory region conferring muscle specific activity of the myoD-CAT reporter gene in the mouse cells was localized using deletion mutants to an element between −7 kb and −4 kb (FIGS. 4A-B). This element was functional only following stable integration but was not functional in transient assays. The sequence entitled "KX FRAG MYOD ENHANCER" is 1978 nucleotides spanning the region between an Apa I site and a Xho I site at approximately −5870 and −3892 nucleotides upstream from the major start site of myoD gene transcription. The results of additional deletion analysis demonstrate that the necessary region of the enhancer lies between approximately −5390 and −4670, i.e., between positions 421 and 1200 of the sequence represented in FIG. 4A (see FIG. 4A). However, it is noted that this larger regulatory region also includes other nucleotide sequence motifs that will most likely provide important additional regulatory elements. These regulatory sequence motifs represent:

1. two sequences approximating MEF2 binding sites, i.e., *7; *12; positions 312 to 321 and 1097 to 1105, FIG. 4A;
2. sequences representing consensus binding sites for helix-loop-helix regions in regulatory trans-acting bHLH proteins such as MyoD, i.e., *5; *9, *10, *11; positions 265 to 270, 486 to 491, 608 to 613, and 741 to 746, FIG. 4A;
3. an M-CAT binding site similar to that described in FIG. 2A, i.e., *3; positions 163 to 169, FIG. 4A;
4. an AP1 binding site, i.e., *4; positions 254 to 260, FIG. 4A;
5. an SP1 binding site similar to that described in FIG. 2A, i.e., *6; positions 291 to 297, FIG. 4A; and,
6. a CArG Box or SRF site, i.e., *8; positions 467 to 476, FIG. 4A.

An analysis of myogenesis (myotube, "Tubes"; and myoblast, "Blasts") in mouse myocyte C2C12 cells shows that both the DRR enhancer and the PRR promoter regions are required to achieve expression (i.e., "C1", FIG. 2). The results with CAAT are similar to the results obtained with primary chick muscle cultures (above), wherein deletion of the CAAT binding sequence in the proximal regulatory region (PRR) resulted in a significant decrease in CAT activity expressed from a DRR-containing myoD-CAT construct.

In contrast to the myogenic activity of the myoD-CAT constructs in myoblasts and myotubes, i.e., described above, stable integrants of these constructs in non-myoblastic 10T1/2 cells were inactive, similar to the inactivity observed for the endogenous 10T1/2 myoD gene in these cells. Since it is known that the endogenous 10T1/2 myoD gene can be activated either by treatment with 5-azacytidine or by forced expression of a transfected MyoD cDNA, this method of auto-activation was tested to see how this auto-activation of myogenesis affected expression from the regulatory sequences. To investigate the regulatory effects operative during azacytidine-induced autoactivation, a polyclone of 10T1/2 cells that had been transfected with the 7 kb myoD-CAT DRR reporter construct was converted to myoblasts either by treatment with azacytidine or infection with a MyoD expressing retrovirus, and then CAT expression was evaluated. In the case of both azacytidine and retrovirus infection, the 7 kb myoD-CAT construct was activated coincident with the activation of the endogenous myoD gene. We conclude from these experiments that the 7 kb myoD-CAT DRR construct contains the requisite nucleotide sequence and elements sufficient for auto-regulation, since in each case the CAT activity was coincident with the expression of the endogenous myoD gene; however, the results do not allow us to distinguish between auto-activation and de novo activation.

EXAMPLE 6

Investigation of Possible Additional Cis Regulatory Regions

The experiments above demonstrate that the distal and proximal regulatory elements, i.e., DRR and PRR, confer myoblast-specific activity on a reporter construct and that these regulatory regions alone appear sufficient for a) expression of myogenic activity in murine myoblasts and myotubes and b) auto-regulation in 10T1/2 cells, i.e., the ability of the cells to up-regulate MyoD expression in the presence of environmental challenges such as 5'azacytidine or exogenous MyoD expression. However, the inactivity of the 7 kb myoD-CAT DRR constructs in mouse non-myoblastic 10T1/2 cells, i.e., prior to the activation of the endogenous gene, was considered. It was reasoned that either unknown cis- or other transacting elements might account for "triggering" of auto-activation, or alternatively, triggering might be quantitative, i.e., with small amounts of MyoD (or MyoD mRNA) being produced which feed-back and induce additional MyoD expression. In the latter case, our CAT reporter gene constructs might not be capable of autoregulation because the transcribed product was CAT instead of MyoD. If this were the case, then transfection of 10T1/2 cells with myoD genomic fragments that contained both the DRR and PRR driving the MyoD coding region might be sufficient to convert them to myoblasts without the requirement for exogenous environmental agents. Therefore, 10T1/2 cells were cotransfected with a) the selectable marker for neomycin resistance driven by a viral LTR and b) a genomic fragment of myoD extending from −12.0 kb to several hundred nucleotides past the poly-A site; this region included the entire DRR and PRR plus the coding region with the presumptive poly-A site. A control vector was also made to test the functional integrity of the coding region and poly-A site of the genomic constructs by cloning the MSV-LTR upstream of the MyoD coding region. Clones of stable transfectants were selected in G418 and switched to differentiation medium to score for myogenesis. While the MSV-LTR-driven genomic sequence yielded muscle colonies at a frequency similar to transfection with the LTR-driven cDNA, the genomic colonies had only a few scattered muscle cells. This finding would be consistent with either the absence of the appropriate trans-acting regulatory factor(s) or the lack of all the necessary cis acting regulatory elements. Similar experiments were therefore conducted wherein 10T1/2 cells were transfected with the entire cosmids from which the genomic clones were derived. Similar results were recorded. These genomic cosmids contained as much as 20 kb both 5-prime and 3-prime to the gene, suggesting that any putative cis regulatory elements sufficient for activity in 10T1/2 cells would have to be either (i) very distant from the gene (i.e., >20 kb), (ii) deleted from the genomic cosmid constructs, e.g., by rearrangements, or (iii) silenced by a cis modification, e.g., following transfection, or (iv) represented as a general polymorphism-conferring function in the C3H strain but not in A/J strain of mouse. Thus, while not ruling out the presence of additional cis regulatory elements, these combined results support the notion that the major regulatory elements controlling myoD gene expression are trans-acting regulatory elements which exert their effects upon elements in the PRR and DRR 5′ regions of the myoD gene.

In light of the above, the 40 nucleotide region of the myoD PRR that is necessary for muscle-specific activity contains the SP1, M-CAT, and CAAT binding motifs. SP1 sites are reportedly found in other muscle-specific regulatory regions, e.g., the alpha cardiac actin promoter, and are thought to represent general activation transcription factors without cell type specificity. The gel shifts with SP1 sequences from the myoD PRR (above) are consistent with the interpretation that a ubiquitously expressed factor binds to this site.

The M-CAT binding sequence was reported in the Troponin I promoter. In that case two intact M-CAT sites are necessary for expression of this gene in muscle cells. In gel retardation assays using an M-CAT oligo the results suggest that only a minor fraction of the shifted material can be attributed to M-CAT binding.

CAAT boxes are reportedly found in the promoters of many genes and are often incorporated into a CArG box in muscle promoters. The CArG box is a $CC(A/T)_6GG$ sequence that binds SRF and other factors. While the CAAT box in the myoD PRR is not incorporated into a CArG box, it is part of a $CC(A/T)_4GG$ motif, which, while similar to a CArG box, has not been described as having any functional relevance in other muscle genes. The CAAT box binding protein CEBP has been reported to be important for the tissue-specific expression of genes in adipocytes. The suppression of CAAT box binding activity in BrdU substituted chick myoblasts (above) raises the possibility that BrdU inhibits MyoD transcription and myogenesis in chick cells by inhibiting the transcription of this factor. Since CAAT box binding proteins are reportedly necessary for tissue-specific transcription in other cells types, it is possible that BrdU may inhibit the expression CAAT binding proteins that are involved in the transcriptional activation of regulatory genes. BrdU does not inhibit CAAT binding factors in mouse cell lines and therefore locating the region of the myoD regulatory sequences that respond to BrdU in mouse cells will define an important regulatory domain.

The fourth sequence motif present in the PRR is the TATA box. The sequence of the TATA box is conserved in the Xenopus and chicken myoD gene. This strong conservation of sequence makes it plausible that the TATA element may confer some muscle specificity, e.g., such as has been reported for the myoglobin and chicken cardiac actin genes.

The fifth region of interest is the MyoD binding sites upstream from the PRR. While deletion of these sites does not affect gene expression in a transient assay in primary chick muscle cells, the ability of the sites to act as a regulatory region responsive to trans-activation by MyoD can be demonstrated when they are joined to the TK promoter or the MCK promoter. It is likely that these MyoD binding sites modulate activity in a manner that is not necessary in chick muscle cells.

The DRR is necessary in addition to the PRR for muscle-specific activity in mouse muscle cell lines. Overlapping deletions of the 5-prime region of the myoD gene were useful in mapping a necessary region of the DRR between approximately −5390 bp and −4670 bp. An unusual feature of the DRR is the requirement for integration to achieve enhancer activity. While this requirement for integration is also reportedly true for the hemoglobin LAR, in neither case is there an understanding of the role integration plays in regulating the activity of these regions. At this time it is only possible to speculate on why the myoD DRR is relatively inactive in transient assays: i) The factors interacting with the DRR may be in very limited supply and transient assays may titrate-out the available factors. This interpretation presupposes the independent binding of two or more factors. ii) The DRR may be insufficient for activity by itself, but integration near a second necessary element may permit activity. Since approximately 50% of stable colonies show activity, any such putative additional regulatory element would have to be frequently represented in the genome. iii) Chromatin structure may be necessary to expose regulatory domains. iv) It may be necessary to remove bacterial methylation patterns that could interfere with factor binding.

A second curious feature of the DRR is that it is required for PRR activity in mouse muscle, but not in chick muscle. In part, this may have to do with a higher abundance of activation factors in chick, but it could also reflect a different strategy of regulating MyoD expression. Since both C2C12 myoblasts and 10T1/2 cells contain abundant amounts of SP1 and CAAT binding factors, but do not activate transcription without the DRR, it is reasonable to conclude that simple abundance of the identified factors is not the limiting step in transcriptional activation.

Neither the myoD-CAT constructs nor the myoD genomic sequences demonstrate significant activity when transfected into 10T1/2 cells. In most aspects, the activity of the transfected CAT constructs closely match the activity of the endogenous gene. Both the myoD-CAT constructs and the endogenous gene are inactive in 10T1/2 cells, but can be activated either by expression of an exogenous MyoD or by treatment with 5-azacytidine, although it is possible that the latter might be activating the CAT construct through the activity of the endogenous MyoD. Another similarity between the myoD-CAT constructs and the endogenous myoD gene is that they are both activated by MyoD in the presence of either high serum or TGF-Beta. This is in sharp contrast to other defined muscle-specific enhancers for which serum and TGF-Beta reportedly act to inhibit the activity of MyoD.

EXAMPLE 7

Muscle Specificity of MyoD Regulatory Regions

The specificity of the myoD regulatory regions was investigated in mouse C2 muscle cells or 10T1/2 fibroblasts transfected with either the −7 kb myoD-CAT regulatory construct or a −4 kb myoD-CAT regulatory construct. Stable integrants were selected and approximately 1000 such clones were pooled and analyzed for CAT activity. The results presented in Table 1, below, show substantially background levels of activity in fibroblasts and significant activity in muscle cells.

TABLE 1

Relative Activity of myoD-CAT Constructs in Muscle Cells and Fibroblasts

| CAT VECTOR | CELL TYPE | |
| --- | --- | --- |
| | Muscle Cell CAT* | Fibroblasts CAT* |
| −7KB CAT | $5.2 \times 10^4$ | $<1 \times 10^3$ |
| −4KB CAT | $<1 \times 10^3$ | $<1 \times 10^3$ |

*CAT: CAT activity as determined by cpm with a background level of 1,000.

EXAMPLE 8

The myoD Regulatory DNA and RNA in Retroviral Expression Vectors

The isolated myoD gene regulatory DNA sequences encompassing the PRR and DRR sequences were utilized to construct two retroviral expression vectors, termed "LHDMDN.NSA" (i.e., containing 1445 bp of myoD regulatory sequence) and "LHDMDN.531" (i.e., containing 2244 bp of myoD regulatory sequence). Both vectors have the same myoD regulatory sequence, both contain the PRR and DRR sequences, and both were found to have the same functional activity. For purposes of simplicity, only the "LHDMDN.531" vector has been deposited with the American Type Culture Collection, Rockville, Md.

The construction of retroviral vectors containing myoD regulatory RNA will now be described.

The test vectors, LHDMDN.531 and LHDMDN.NSA, consisting of a standard Moloney Murine Leukemia Virus (MoMLV) backbone that carry two selectable markers: namely, (1) the enzyme Histidinol Dehydrogenase (hisD; "HD"), conferring drug resistance to L-histidinol; and, (2) the enzyme Neomycin Phosphotransferase (neo; "N"), conferring resistance to the neomycin analogue G418. The hisD gene in the construct is under the regulatory control of the promoter region in the MoLV long terminal repeat sequences (LTR; "L"), while the neogene was placed under the control of the myoD PRR and DRR regulatory sequences containing the 5' enhancer and promoter regions of the myoD gene (ME)P; "MD"). The LTR promoter is operative in directing expression of downstream genes in a wide variety of cell types, while MDP directs preferential expression of downstream genes in early replicating myoblasts. The arrangement of these two marker genes in the construct allows ubiquitous expression of HisD, i.e., as a selectable marker in both muscle cells and non-muscle cells, e.g., in fibroblasts. The MDP driven neogene is used as a muscle-specific selectable marker. (Materials and methods of these constructions, infections of cells, and assays for marker enzymes in cells are described below in the section entitled "Materials and Methods".)

Although retroviral particles will efficiently deliver vector sequences into the genome of a target cell, a drug-resistance phenotype is only induced if the selectable marker gene is expressed at a sufficiently high level following integration. The relative titer of a virus preparation depends in part on the level of expression achieved in successfully infected target cells. Thus, if exceedingly high levels of drug are used, none of the infected cells will express sufficient amounts of the drug resistance gene marker to counter the high selective pressure. In the case of the LHDMN vectors, expression of the hisD gene from the LTR should provide sufficient gene product in both muscle and non-muscle cells to exhibit reasonably high titers under L-histidinol selection. On the other hand, the MDP driven neogene should express less neogene product in non-muscle cells than in muscle cells. This should allow for the preferential selection of muscle cells under sufficiently stringent selective conditions.

To test whether the LHDMDN vectors expressed the MDP driven neo gene in a muscle specific manner, C2C12 mouse muscle cells (C2) and NIH3T3 mouse fibroblasts (3T3) were infected with limiting dilutions of LHDMDN virus. Both the 531 and NSA forms of LHDMDN were used and the infected cells were selected in L-histidinol or in G418. Table 2 shows the relative titers of four representative virus producer clones and compares the levels of infection in muscle and non-muscle cells (ratio of the C2 viral titers to the 3T3 viral titers).

TABLE 2

LHDMDN Titers and Relative Infection Rates for Muscle and Non-Muscle Cells

| | L-histidinol (LTR) | | | G418 (myo-D) | | |
| --- | --- | --- | --- | --- | --- | --- |
| | NIH 3T3 | C2 | C2/3T3* | NIH 3T3 | C2 | C2/3T3* |
| LHDMDN.NSAc2 | $5 \times 10^4$ | $1 \times 10^5$ | 2 | $4 \times 10^3$ | $8 \times 10^5$ | 200 |
| LHDMDN.NSAc6 | $1 \times 10^5$ | $1 \times 10^5$ | 1 | $2 \times 10^3$ | $4 \times 10^5$ | 200 |
| LHDMDN.531c3 | $4 \times 10^5$ | $3 \times 10^5$ | 7.5 | $2 \times 10^3$ | $4 \times 10^5$ | 200 |
| LHDMDN.531c5 | $8 \times 10^5$ | $3 \times 10^5$ | 3.8 | $2 \times 10^3$ | $6 \times 10^5$ | 300 |

*C2/3T3: ratio of the viral titer with C2 cells divided by the viral titer of 3T3.

Under the selective conditions used here (i.e., 8 mM L-histidinol; 1.5 mg/ml G418), a clear tissue-specific differential expression of G418 resistance can be seen with 200–300-fold higher titers in muscle cells than in fibroblasts (ratio C2/3T3). For comparison, L-histidinol selection of myoblasts or fibroblasts shows at most a 7.5 fold difference between muscle cells and fibroblasts (ratio C2/3T3). This suggests that the MDP expression elements were able to provide muscle-specific enhanced gene expression in a cell and further that the elements were preserved in an operative fashion while integrated in the genome in a retroviral context.

To more closely examine the difference in neo expression in muscle cells and fibroblasts, the specific activity of neomycin phosphotransferase (NPT) was determined for both the C2 and 3T3 cells infected with the LHDMDN.NSA vector. As a positive control for NFT activity, cells were infected with the LHDSN vector an selected in parallel. LHDSN is identical to LHDMDN except that the neogene expression is controlled by the strong SV40 promoter which is active in both myoblasts and fibroblasts. Table 3 lists the activity of NPT found in bulk populations of LHDMDN.NSA- or LHDSN-infected C2 and 3T3 cells which were selected in L-histidinol.

TABLE 3

NPT Activity in Muscle and Non-Muscle Cells Infected with LHDMDN or LHDSN

|  | NSA | SV40 | NSA/SV40* |
|---|---|---|---|
| C2 | 3.7 | 4.9 | 0.8 |
| 3T3 | 1.6 | 6.4 | 0.3 |
| C2/3T3** | 2.3 | 0.8 |  |

*NSA/SV40: ratio of NPT activity (CPM/min/mg protein ($\times 10^{-3}$) with LHDMDN.NSA (NSA) to that with LHDSN (SV40).
**C2/3T3: ratio of NPT activity (CPM/min/mg protein ($\times 10^{-3}$) with LHDMDN.NSA (NSA) or LHDSN (SV40) in C2 or 3T3 cells, respectively.

Comparison of SV40 mediated NPT activity with the activity of MDP expressed neo shows that the MDP enhancer-promoter produces nearly as much NFT activity as SV40 in C2 cells (i.e., 80% of SV40 values) while in 3T3 fibroblasts MDP produces about one-third of the NPT activity of SV40. When comparing MDP directed NPT activity in C2 vs. 3T3 cells, a two-fold difference is seen, again showing the cellular-specificity of the regulatory effects of the MDP elements. It is worthy of note that although both comparisons of NFT activity clearly show that the MDP elements are preferentially expressed in muscle cells, the differences with retroviral constructs were actually lower than expected based on transfection analyses (above) wherein differences of 20- to 50-fold between expression in C2 muscle cells and 10T1/2 fibroblasts were common observed using NSA MDP. One possible explanation for this effect of retroviral vectors is that the strong enhancer elements in the viral LTR act at a distance to promote expression from the MDP promoter in non-muscle cells, i.e., in the controls.

EXAMPLE 9

Selection of Muscle Cells Using myoD Regulatory DNA and RNA

PA317 cells (a derivative fibroblast cell line) were transduced with EMC11.S, a plasmid containing an RSV promoter driving expression of MyoD protein coding sequences. When exogenous MyoD protein is expressed in fibroblasts it induces expression of a number of myoD-regulatable proteins in the fibroblasts and thus yields cells that are permissive for MDP enhancer-promoter directed gene expression.

A clone of myoD transducer PA317 cells which expressed high levels of MyoD protein, PAMD308, was chosen for use in further studies. To test that the PAMD308 cells were permissive for MDP-directed expression, LHDMDN virus, (i.e., wherein the viral LTR drives ubiquitous expression of histidinol resistance but the myoD regulatory DNA drives expression of muscle-specific expression of neomycin-resistance), was used to infect PA317 cells and PAMD308 cells. The number of L-histidinol was compared with the number of G418 resistant colonies. Table 4 shows the ratio of L-histidinol or G418 resistant colonies in PAMD308 vs. PA317 cells. Little difference is seen between the cell lines with L-histidinol selection (1–3.4-fold higher titer on PAMD308 cells). In contrast, selection with G418 shows a 100–500-fold increase in infection rate when myoD protein is present. This demonstrates an enhanced expression level of the MDP enhancer-promoter in the presence of MyoD protein, and shows that in the presence of MyoD there is selection for muscle cells, i.e., for cells that are resistant to G418 because of their expression of MyoD.

TABLE 4

Ratio of LHDMDN Drug Resistant Colonies in PAMD308 vs. PA317 Cells

|  | L-Histidinol | G418 |
|---|---|---|
| LHDMDN.531 | 1 | 135 |
| LHDMDN.NSA | 3.4 | 510 |

Materials and Methods

Retroviral Vectors pLHDMDN was constructed by removing the SV40 promoter from pLHDSN (30) and replacing it with sequences containing the myoD PRR and DRR enhancer-promoter elements. Two vectors were constructed using MDP sequences which conferred muscle specific expression in transfection studies. The two MDP elements were termed "531" and "NSA". The resulting plasmids containing each vector were termed pLHDMDN.531 and pLHDMDN.NSA.

LHDMDN Virus Producing Cell Lines

Cell lines producing LHDMDN.531 or LHDMDN.NSA virus were isolated using standard techniques (31) involving transfection of the vector construct into PE501 cells followed by infection of PA317 cells with transiently expressed virus from the PE501 cells. Infected PA317 cells were selected in L-histidinol and the resulting drug resistant clones were tested for LHDMDN virus production.

Infection and Selection

Infection protocols were conducted essentially as described previously (31). Briefly, virus containing medium was harvested from producer cells and was used in limiting dilution analyses to infect target C2 (muscle) or 3T3 (fibroblast) cells which had been plated at a density of $5 \times 10^5$ cells per 6 cm dish on the previous day. After 24 hrs. of exposure to virus, the target cells were treated with trypsin and 1/10th and 1/50th of the cells were replaced in the presence of the selective drug. The concentration of drugs used for selection was 4 mM L-histidinol or 1.5 mg/ml G418 (50% active) for both the C2 and 3T3 cell cultures. In later assays, the L-histidinol was increased to a concentration of 8 mM to facilitate selection of the more resistant C2 cells.

Relative titers (i.e., of virus) remained the same with this increase in drug concentration.

Neomycin Phosphotransferase Assays

The activity of the neogene product, neomycin phosphotransferase (NPT), was determined as follows: briefly, 5 ug total soluble cellular protein (i.e., in a cellular extract) was incubated for 30 minutes at 37° C. in the following reaction mixture: 67 mM Tris-Maleate pH 7.1, 42 mM $MgCl_2$, 400 mM $NH_4Cl$, 1 uM rATP/gamma$^{32}$P-rATP, 0.5 mM neomycin sulfate. The reaction was stopped by phenol extracting the reaction mixture and aliquots of the aqueous phase were spotted onto P-81 ion exchange paper. The paper was extensively washed and $^{32}$P CPM determined. NPT activity is expressed as the CPM incorporated into neomycin sulfate per ug soluble protein per minute.

Citations

1. Lassar, A. B. et al. 1989. Cell 58: 823.
2. Davis, R. L. et al. 1987. Cell 51: 987.
3. Wright, W. E. et al. 1989. Cell 56: 607.
4. Edmonson, D. G. et al. 1989. Genes Dev. 3: 628.
5. Braun, T. et al. 1989. EMBO J. 8: 701.
6. Rhodes, S. J. et al. 1989. Genes Dev. 3: 2050.
7. Miner, J. H. et al. 1990. Proc. Natl. Acad. Sci. USA 87: 1089.
8. Braun, T. et al. 1990. EMBO J. 9: 821.
9. Weintraub, H. R. 1990. Proc. Natl. Acad. Sci. USA 87: 5623.
10. Piette, J. et al. 1990. Nature 345: 353.
11. Rosenthal, N. et al. 1990. Nucleic Acids Res. 18: 6239.
12. Sartorelli, V. 1990. Genes Dev. 4: 1811.
13. Murre, C. et al. 1989 Cell 58: 537.
14. Brennan, T. J. 1990. Genes Dev. 4: 582.
15. Davis, R. L. et al. Cell 60: 733.
16. Sun, X. H. et al. 1991. 64: 459.
17. Henthorn, P. et al. 1990. Science 247: 467–470.
18. Blackwell, T. K. et al. 1990. Science 250: 1104.
19. Davis, R. & H. Weintraub unpublished observations.
20. Schafer, B. W. et al. 1990. Nature 344: 454.
21. Benezra, R. et al. 1990. Cell 61: 49–59.
22. Lassar, A. B. et al. 1989. Cell 58: 659.
23. Sasson, D. et al. 1989. Nature 341: 303.
24. Sorrentino, V. R. et al. 1990. Proc. Natl. Acad. Sci. USA 87: 8442.
25. Weintraub, H. et al. 1989. Proc. Natl. Acad. Sci. USA 86: 5434.
26. Choi, J. et al. 1990. Proc. Natl. Acad. Sci. USA 87: 7988.
27. Thayer, M. et al. 1990. Cell 63: 23.
28. Ptashne, M. et al. 1990. Nature 346: 329.
29. Lin, A. Y. et al. 1989. Gene Dev. 3: 986.
30. Stockschalecler, M. et al. 1991. Human Gene Therapy 2: 33–39.
31. Miller, A. D. et al. 1986. Mol. Cell. Biol. 6: 2895.

While the preferred embodiment of the invention has been illustrated and described, it will be appreciated that various changes can be made therein without departing from the spirit and scope of the invention.

---

The embodiments of the invention in which an exclusive property or privilege is claimed are defined as follows:

1. An isolated DNA or RNA molecule comprising a myoD proximal regulatory region capable of hybridizing under stringent conditions to the nucleotide sequence from positions 590 to 883 in SEQ ID NO: 1.

2. The isolated DNA or RNA molecule of claim 1, consisting essentially of both a first nucleotide sequence shown from positions 732 to 722 in SEQ ID NO: 1 and a second nucleotide sequence shown at positions 802 to 837 in SEQ ID NO: 1.

3. An isolated DNA or RNA molecule comprising a myoD distal regulatory region capable of hybridizing under stringent conditions to the nucleotide sequence from positions 1 to 1200 in SEQ ID NO: 2.

4. The isolated DNA or RNA molecule of claim 3, consisting essentially of the nucleotide sequence shown from positions 421 to 1200 in SEQ ID NO: 2.

5. A DNA or RNA expression vector for introducing a gent into a cell, comprising a myoD regulatory region operably linked to a gene whereby transcription of the gene is controlled by the myoD regulatory region when the vector is stably integrated into the genome of the cell, wherein the myoD regulatory region comprises a distal regulatory region and a proximal regulatory region, wherein the distal regulatory region comprises DNA or RNA capable of hybridizing under stringent conditions to the nucleotide sequence shown from positions 421 to 1200 in SEQ ID NO: 2, and wherein the proximal regulatory region comprises DNA or RNA capable of hybridizing under stringent conditions to both a first nucleotide sequence shown from positions 732 to 772 in SEQ ID NO: 1 and a second nucleotide sequence shown at positions 802 to 837 in SEQ ID NO: 1.

6. A cell transduced or transfected with the expression vector of claim 5.

7. The cell of claim 6, wherein the cell is selected from the group consisting of: pre-muscle cells, muscle cells, myocytes, myoblasts, and cells genetically engineered to express MyoD protein.

8. In a method of inducing a muscle phenotype in a non-muscle cell, comprising the step of introducing a MyoD coding sequence into the non-muscle cell, the improvement comprising operably linking a myoD regulatory region to the MyoD coding region whereby transcription of the MyoD coding region is controlled by the myoD regulatory region when the vector is introduced into the cell, wherein the myoD regulatory region comprises a distal regulatory region and a proximal regulatory region, wherein the distal regulatory region comprises DNA or RNA capable of hybridizing under stringent conditions to the nucleotide sequence shown from positions 421 to 1200 in SEQ ID NO: 2, and wherein the proximal regulatory region comprises DNA or RNA capable of hybridizing under stringent conditions to both a first nucleotide sequence shown from positions 732 to 772 in SEQ ID NO: 1 and a second nucleotide sequence shown at positions 802 to 837 in SEQ ID NO: 1.

9. A method of positively selecting for muscle cells, comprising:
constructing a DNA or RNA expression vector comprising a myoD proximal regulatory region and a myoD distal regulatory region both operably linked to a marker gene whereby transcription of the marker gene is controlled by the myoD proximal and distal regulatory regions,
introducing the expression vector into the genomes of a population of cells, and
positively selecting for cells that express the marker, wherein the myoD proximal regulatory region is DNA or RNA capable of hybridizing under stringent conditions to the nucleotide sequence shown from positions 590 to 883 in SEQ ID NO: 1 and wherein the myoD distal regulatory region is DNA or RNA capable of hybridizing under stringent conditions to the nucleotide sequence shown from positions 1 to 1200 in SEQ ID NO: 2.

10. A method of negatively selecting for a muscle cell, comprising:
constructing a DNA or RNA expression vector comprising a myoD proximal regulatory region and a myoD distal regulatory region both operably linked to a gene encoding a toxin whereby transcription of the gene is controlled by the myoD proximal and distal regulatory regions, and
introducing the vector into the genome of the cell, wherein the myoD proximal regulatory region is DNA or RNA capable of hybridizing under stringent conditions to the nucleotide sequence shown from positions 590 to 883 in SEQ ID NO: 1 and wherein the myoD distal regulatory region is DNA or RNA capable of hybridizing under stringent conditions to the nucleotide sequence shown from positions 1 to 1200 in SEQ ID NO: 2.

11. A method of negatively selecting for muscle cells, comprising:
introducing a DNA or RNA expression vector into the genomes of a population of cells, the expression vector comprising a myoD proximal regulatory region and a myoD distal regulatory region both operably linked to a gene encoding a protein for converting a prodrug to a toxic drug whereby transcription of the gene is controlled by the myoD proximal and distal regulatory regions, and
contacting the cells with the prodrug,
wherein the myoD proximal regulatory region is DNA or RNA capable of hybridizing under stringent conditions to the nucleotide sequence shown from positions 590 to 883 in SEQ ID NO: 1 and wherein the myoD distal regulatory region is DNA or RNA capable of hybridizing under stringent conditions to the nucleotide sequence shown from positions 1 to 1200 in SEQ ID NO: 2.

12. An isolated DNA or RNA molecule comprising a myoD distal regulatory region capable of hybridizing under stringent conditions to the nucleotide sequence from positions 1 to 1978 in SEQ ID NO: 2.

13. The isolated DNA or RNA molecule of claim 12, consisting essentially of the nucleotide sequence shown from positions 421 to 1978 in SEQ ID NO: 2.

* * * * *

UNITED STATES PATENT AND TRADEMARK OFFICE
CERTIFICATE OF CORRECTION

PATENT NO. : 5,352,595
DATED : October 4, 1994
INVENTOR(S) : Tapscott et al.

It is certified that error appears in the above-identified patent and that said Letters Patent is hereby corrected as shown below:

| COLUMN | LINE | | |
|---|---|---|---|
| Title Page, item [56] | Other Pubs | "Tabscott" should read --Tapscott-- | |
| 1 | 7 | "fights" should read --rights-- | |
| 2 | 23 | "Coy" should read --(by-- | |
| 2 | 25 | "EA7," should read --E47,-- | |
| 5 | 6 | "myroD" should read --myoD-- | |
| 5 | 6 | Delete "gene;" and insert --gene (SEQ ID NO:2);-- | |
| 5 | 18 | "HisD" should read --HisD, myoD-- | |
| 5 | 21 | "schematiclaly" should read --schematically-- | |
| 5 | 51 | "7 kb" should read --7kb-- | |
| 7 | 48-49 | "transducer" should read --transduced-- | |
| 7 | 52 | "(ii)production" should read --(ii) production-- | |

UNITED STATES PATENT AND TRADEMARK OFFICE
CERTIFICATE OF CORRECTION

PATENT NO. : 5,352,595

DATED : October 4, 1994

INVENTOR(S) : Tapscott et al.

It is certified that error appears in the above-identified patent and that said Letters Patent is hereby corrected as shown below:

| COLUMN | LINE | |
|--------|------|---|
| 10 | 13 | "FAGS" should read --FACS-- |
| 24 | 24 | "Stockschalecler," should read --Stockschaleder,-- |
| 27 | 18 | "Figures 4A a" should read --Figures 4A and 4B-- |
| 29 | 17 | "Y" should read --$Y^+$-- |
| 43 | 63 | "722" should read --772-- |
| 43 | 63 | "gent" should read --gene-- |

Signed and Sealed this

Seventh Day of February, 1995

Attest:

BRUCE LEHMAN

*Attesting Officer*      *Commissioner of Patents and Trademarks*

SEQUENCE LISTING ( 1 ) GENERAL INFORMATION:

( i i i ) NUMBER OF SEQUENCES:4

( 2 ) INFORMATION FOR SEQ ID NO:1:

( i ) SEQUENCE CHARACTERISTICS:
    ( A ) LENGTH:3636 base pairs
    ( B ) TYPE:nucleic acid
    ( C ) STRANDEDNESS:single
    ( D ) TOPOLOGY:linear ( i i ) MOLECULE TYPE:genomic DNA
    ( A ) DESCRIPTION:myoD Genomic;
       proximal regulatory region myoD gene;
       Figures 1A, 1B, and 1C.

( i x ) SEQUENCE DESCRIPTION: SEQ ID NO:1:

```
TCTAGAAGCA  TTCCANGTTC  ACTCAGAGCA  AGATGGNAAC  CCATAGCACA  GGTTTTCTTC   60

TTCTCGGCAG  AAACAGATCA  ACCTAGACCC  CCATGGGTCT  CNTAGACACT  CACAGAAAGT  120

AAGTTGGAGG  GAGCCTCCCT  CTCTCTCCCT  CCCTCTTTTC  CTTGGACTGT  CCACCCGGAG  180

TTTGAGCAGA  ATGGCTTGAA  GTTTTAATGA  TGATTCCCAC  TACGCATGCA  AGGACAGCGC  240

TGGGTTCTAA  GCTTCCCGTG  GAAGAACAGA  TATTCTCTGA  GCCATTCCCA  GATGGAGAAT  300

GACCAAATAG  CACTGCCACC  GATCATTTGT  GCCAGGCTTG  CTCACCTAGA  CCTTCTGAGT  360

CTCACTGTCT  CTTGCCCACT  TTGTCCTTGG  CTCAACTTCT  CTGGGTGTGT  CATCATTTCT  420

CCACTCTTCT  CTAGAACTTT  CATTGTCCCG  TAGCCTTGAG  TCTCTCTCCA  AACCTCCTGC  480

AATCTGATTT  CTAACTCCTA  TGCTTTGCCT  GGTCTCCAGA  GTGGAGTCCG  AGGTCAGCTC  540

CGAAGTGAGC  ACTGAGGTCA  GTACAGGCTG  GAGGAGTAGA  CACTGGAGAG  GCTTGGGCAG  600

GCTGCACCAG  ATAGCCAAGT  GCTACCGCGT  ATGGCTGCCA  GTCTCTCTGC  CCTCCTTCCT  660
```

```
AGCTAGGCAG CTGCCCCAGC ACAGAGTCGC GGGAGGGGGC ACTCCCTGGC CCCAGTGGCT  720
ACCCTGGGGA CCCCAAGCTC CGCCCTACTA CACTCCTATT GGCTTGAGGC GCCCCGCCC   780
CCAGCCTCCC TTTCCAGCTC CCGGGCTTTT AGGCTACCCT GGATAAATAG CCCAGGGCGC  840
CTGGCGCGAA GCTAGGGGCC AGGACGCCCC AGGACACGAC TGCTTTCTTC ACCACTCCTC  900
TGACAGGACA GGACAGGGAG GAGGGGTAGA GGACAGCCGG TGTGCATTCC AACCCACAGA  960
ACCTTTGTCA TTGTACTGTT GGGGTTCCGG AGTGGCAGAA AGTTAAGACG ACTCTCACGG 1020
CTTGGGTTGA GGCTGGACCC AGGAACTGGG ATATGGAGCT TCTATCGCCG CCACTCCGGG 1080
ACATAGACTT GACAGGCCCC GACGGCTCTC TCTGCTCCTT TGAGACAGCA GACGACTTCT 1140
ATGATGACCC GTGTTTCGAC TCACCAGACC TGCGCTTTTT TGAGGACCTG GACCCGCGCC 1200
TGGTGCACAT GGGAGCCCTC CTGAAACCGG AGGAGCACGC ACACTTCCCT ACTGCGGTGC 1260
ACCCAGGCCC AGGCGCTCGT GAGGATGAGC ATGTGCGCGC GCCCAGCGGG CACCACCAGG 1320
CGGGTCGCTG CTTGCTGTGG GCCTGCAAGG CGTGCAAGCG CAAGACCACC AACGCTGATC 1380
GCCGCAAGGC CGCCACCATG CGCGAGCGCC GCCGCCTGAG CAAAGTGAAT GAGGCCTTCG 1440
AGACGCTCAA GCGCTGCACG TCCAGCAACC CGAACCAGCG GCTACCCAAG GTGGAGATCC 1500
TGCGCAACGC CATCCGCTAC ATCGAAGGTC TGCAGGCTCT GCTGCGCGAC CAGGACGCCG 1560
CGCCCCCTGG CGCCGCTGCC TTCTACGCAC CTGGACCGCT GCCCCCAGGC CGTGGCAGCG 1620
AGCACTACAG TGGCGACTCA GACGCGTCCA GCCCGCGCTC CAACTGCTCT GATGGCATGG 1680
TAAGGCGGGG GGCTCAGGAG GACGAGCAAT GGAGGCGGCG CCTGGGGTAT CTGCAACAGG 1740
TTTCCGAGGC CCTTGGGGTG GGGGTGTCCC TTATACCTAG ATGCTCCTGG CATCTGACAC 1800
TGGAGTCGCT TTGGAGACCC ATGGGCATCT ATGATNCTGC CGATCGGGGG TGGAACACTG 1860
CTGCGCAGAC CCCGGGATAT GCTTTTCCTT CTCATTATTA CCCTAATGTC AGATTGATTG 1920
TTTCCTGGAG TGACTGTCCA CTCTCAGTTT GGCCCCGCAT GCGACAGCTT CCAGTGTGTG 1980
GCTGGGTCCT ACCACCTGGG GAGCTGACCC AGTCCTGGAA CCAGCAGCTG AGACTAAGGG 2040
AGTGAGGGAG GGGTGATGAC AAGGAGTGTT GCTTGAGACC CACTCGGGCC CTGTAGACCT 2100
AACTCTGTTA TCCTTGCTAT TCGCAGATGG ATTACAGCGG CCCCCCAAGC GGCCCCCGGC 2160
GGCAGAATGG CTACGACACC GCCTACTACA GTGAGGCGGC GCGCGGTGCG TATTCTCAGC 2220
TGTTCCCAGC TAGCAGGCCT TATCGGCNTT CTGTATCCCC CTTGAAACTT TCCTCGCTCC 2280
TAGGCTTAGT ATCCTTCCTC CTGCCTCACC ACATACATAC CCGTACCTTG GGATGGCGGG 2340
GGGGGGGGAG GCTGGGGGGG GAGCATTGGG GGAGGGCAAA GAACTATGAT GCACANTTCC 2400
TCTCCTTTCT CCTTCCAGTC TAGCAAGTCC TCAGTTTCCC TTTTCTACAA AGCTCCGTGC 2460
CTATGGGCAG GAGACTTGAG AAGGGCCGCA AGTTTGGATT ACTAACCTTC CACTCCCCTC 2520
ACAGAGTCCA GGCCAGGGAA GAGTGCGGCT GTGTCGAGCC TCGACTGCCT GTCCAGCATA 2580
GTGGAGCGCA TCTCCACAGA CAGCCCCGCT GCGCCTGCGC TGCTTTTGGC AGATGCACCA 2640
CCAGAGTCGC CTCCGGGTCC GCCAGAGGGG GCATCCCTAA GCGACACAGA ACAGGAACC  2700
CAGACCCCGT CTCCCGACGC CGCCCCTCAG TGTCCTGCAG GCTCAAACCC CAATGCGATT 2760
TATCAGGTGC TTTGAGAGAT CGACTGCAGC AGCAGAGGGC GCACCACCGT AGGCACTCCT 2820
GGGGATGGTG CCCCTGGTTC TTCACGCCCA AAAGATGAAG CTTAAATGAC ACTCTTCCCA 2880
ACTGTCCTTT CGAAGCCGTT CTTCCAGAGG GAAGGGAAGA GCAGAAGTCT GTCCTAGATC 2940
CAGCCCCAAA GAAAGGACAT AGTCCTTTTT GTTGTTGTTG TTGTAGTCCT TCAGTTGTTT 3000
GTTTGTTTTT TCATGCGGCT CACAGCGAAG GCCACTTGCA CTCTGGCTGC ACCTCACTGG 3060
GCCAGAGCTG ATCCTTGAGT GGCCAGGCGC TCTTCCTTTC CTCATAGCAC AGGGGTGAGC 3120
```

```
CTTGCACACC TAAGCCCTGC CCTCCACATC CTTTTGTTTG TCACTTTCTG GAGCCCTCCT    3180

GGCACCCACT TTTCCCCACA GCTTGCGGAG GCCACTCAGG TCTCAGGTGT AACAGGTGTA    3240

ACCATACCCC ACTCTCCCCC TTCCCGCGGT TCAGGACCAC TTATTTTTTT ATATAAGACT    3300

TTTGTAATCT ATTCGTGTAA ATAAGAGTTG CTTGGCCAGA GCGGGAGCCC CTTGGGCTAT    3360

ATTTATCTCC CAGGCATGCT GTGTAGTGCA ACAAAAACTT TGTATGTTTA TTCCTCAAGC    3420

GGGCGAGCCT CGAGGCTCGC TCGCTCAGGT GTTGGAAATA AAGACGCTAA TTTATACAAA    3480

GTGGCTCTGG CTTTTCCTAA GGGGATCAGA AAGAAACTCT ACGAACTGGG CGGGCTGTCT    3540

CGCAGCGACC CCTGTAGGTG GCAGAAGGGT AGCACGGAGG CTGGGTAGTG CTGGGTAATG    3600

AAGAAGGGCT GGCAGACCTC CAGCTGTAGG GAATTC                              3636
```

( 2 ) INFORMATION FOR SEQ ID NO:2:

( i ) SEQUENCE CHARACTERISTICS:
        ( A ) LENGTH:1978 base pairs
        ( B ) TYPE:nucleic acid
        ( C ) STRANDEDNESS:single
        ( D ) TOPOLOGY:linear ( i i ) MOLECULE TYPE:genomic DNA
        ( A ) DESCRIPTION:KX fragment MyoD Enhancer;
            distal regulatory region myoD gene; Figures 4A a ( i x ) SEQUENCE DESCRIPTION: SEQ ID NO:2:

```
GGGCCCAGCC ACCAGGATGG TATAGTATAG NATAGATTTT ATTTAGAGCA TAGGGAGGGG      60

AGTCAAGAGG GCAGTAGAGG CAAAGAAAGG AAGAGAGAGG GGAGAGAAG AGAAGTAGAG     120

GTGTAGAGGC TGGCCTTGGA GCACGTGGAG AGAGCAGGGN AAAGGAATGG GGAGAGAGGG    180

NAGAATTGGA AACAGAGAAA GAGCAAGAGA GGATCAAGAG AGCAAGGAGG GGGCAAGCA     240

GCCCNTTTTA TAGTGAGTCA GGCACACCTG GTTGTTGCCA GGTAACTGTG GGGCGGGGNT    300

TAGACACAAA GCTAAAAACA TCCACCACCT AGTTNATCTG CCAGACTCTC AAGGTCCTCG    360

CATACCAGAG CCTGGGGGAA TCCCAGAGGG AGACATGTGA AGGCTCCCTG GACCCTGGT    420

CAGGACNGGA CCATGTCTGT GCCCAGCCNG AGTTCCTCTA GGTCAGCCTA AATTGGCCAG    480

ATCTACACTT GGTGGCAGGC AGTTTCAGGC TTTCTGGGAA GCAAAACTGG CAGAGAACAG    540

AGCAGGATCC TTGAGTTGGG AAAGGAAAGT CTAGGGCCAG AGACTGAACC TGGGGCTGGT    600

CCTGTTCCAC CTGTNCTCCC NGTGGTTTCA TCCTCCAGTC CTTCAGCCCC CTAGACCCAA    660

GCCAGCCATG CAGCCCGCAG TAGCAAAGTA AGAGGCCACA GGTCCAGACT GGGTAGGGCA    720

GAGGTGCCTG AGGCTTGGGG CAGGTGCTAG TTGGATCCGG TTTCCAGAGG CAATATATAT    780

ATAAAGGCTG CTGTTTCCCC GATGGTGCAA CACCCCAGAG CCTAGCCAG ACCAACATTC     840

CTGCCNAAAA GCCAGCTCTC CATTTATAGC ACCTTGGAAG ACTAGCCAAG GGAGCTGAAA    900

TGCAAGGCCT GGAAAGGACA GGGGGAAATC AAAGGGCCAC CTATGGCGGC AGGAGAACTG    960

AGCCTCAGGA TGAGCTGTGT GCTTCTCCAG GTCAGTGGGC CTACAGCCTA AGAGGCCCTG   1020

CATTGAGGGG ACAATGCCTC AGCCCAGAGC CAATGGCACG CTCCAGAAGG GGTGGCTGGG   1080

GGAAGTTTTA GTGACCATAA AATAAAAGC AAGGTTGCAA TCACTTAGAC TCAGCATAAA    1140

ATTTATTTCG GTTTTNTAA ATTATTCGTT TTGTTATTTG TGTGCTTGCT TTGCTTTGCT    1200

TTGTTTGCTC GGGTTTGAGA TAAGAGAGAG AGAGAGAGAG AGAGAGAGAG AGAGAGGGAA   1260

GGAGGGAGGG AGGGAGGGAG GGAGGGAGGG AGGAAGGAAG GAAGGAAGGA AGGAAGGAAG   1320

AAAGAAAGAA AGAAAGAAAG AAAGAAAGAA AGAAAGAAAG AAAGAAAGAA ACTAGATTTG   1380

CACAAGTGGT TTGAAGTGCC TTCCTTGGAG ACACCAGGCA CTGCATAATG AAACAGACTT   1440
```

```
GCTCATTCAT CNGCCGAAGG AATATTTGTG GTGCACCTAG AGAGAGCTGA GCATATTCAG    1500

CTGAGGTTCC AAAAAGGAGG AAGCAATAGC TTCGATCGAA ATCATTACTA ACGACAATTA    1560

CATCCATCNC TGTAGATTTA AGTCAAATGA AAGAGCACTT ATGATGAACC CCACATCCAT    1620

CGGCAGCATA CTGTTGGAAT GTTGCAACCG ACCAATGGGA GAGAGCACGT CCCAGGCAAA    1680

CCAGCCTCTG CTTTGCCTGG GCAGAGGCAG CGTGAGAGCT TGTATGAGTA AGTACCTACA    1740

TAGAGCCCAG GTTTGCTGGA ATAGAATGAC TTGTAGCACA TTTTGCTAAA TTCAAGTATA    1800

AGGATAGAAA TCAAAGAGC CCAAGACTGT TCATTCACTC GCTTGACACT TAAACCACTG     1860

TGCCCGCCGT GGGATCACTG CTGCAGTGGC TTCCGGACAC GCCATGGTGA GCAAAGTACT   1920

CCTATCCATG GTATGCTGGT CTTCGTGTCC CTCGGTGATA ACTGACAAGA TCATTCTC     1978
```

( 2 ) INFORMATION FOR SEQ ID NO:3:

( i ) SEQUENCE CHARACTERISTICS:
        ( A ) LENGTH:9115 base pairs
        ( B ) TYPE:nucleic acid
        ( C ) STRANDEDNESS:single
        ( D ) TOPOLOGY:linear ( i i ) MOLECULE TYPE:Other;plasmid DNA
        ( A ) DESCRIPTION:pLHDMDN-53: 5'LTR (position 1-1159); Y
        ( p o s i t i o n  1 1 5 9 - 1 6 4 0 ); HisD (position 1641-3007);
        Myo-D 531.4 ApaI fragment (position 3008-5248);
        driving neo (position 5249-6117); with a
        3'LTR (position 6118-6823) coupled to a pBR322
        plasmid (position 6824-9115); Figures 7A-7D.

( i x ) SEQUENCE DESCRIPTION: SEQ ID NO:3:

```
GAATTGCTAG CAATTGCTAG CAATTGCTAG CAATTCATAC CAGATCACCG AAAACTGTCC    60

TCCAAATGTG TCCCCCTCAC ACTCCCAAAT TCGCGGGCTT CTGCCTCTTA GACCACTCTA   120

CCCTATTCCC CACACTCACC GGAGCCAAAG CCGCGGCCCT TCCGTTTCTT TGCTTTTGAA   180

AGACCCCACC CGTAGGTGGC AAGCTAGCTT AAGTAACGCC ACTTTGCAAG GCATGGAAAA   240

ATACATAACT GAGAATAGGA AAGTTCAGAT CAAGGTCAGG AACAAAGAAA CAGCTGAATA   300

CCAAACAGGA TATCTGTGGT AAGCGGTTCC TGCCCCGGCT CAGGGCCAAG AACAGATGAG   360

ACAGCTGAGT GATGGGCCAA ACAGGATATC TGTGGTAAGC AGTTCCTGCC CCGGCTCGGG   420

GCCAAGAACA GATGGTCCCC AGATGCGGTC CAGCCCTCAG CAGTTTCTAG TGAATCATCA   480

GATGTTTCCA GGGTGCCCCA AGGACCTGAA AATGACCCTG TACCTTATTT GAACTAACCA   540

ATCAGTTCGC TTCTCGCTTC TGTTCGCGCG CTTCCGCTCT CCGAGCTCAA TAAAAGAGCC   600

CACAACCCCT CACTCGGCGC GCCAGTCTTC CGATAGACTG CGTCGCCCGG GTACCGTAT    660

TCCCAATAAA GCCTCTTGCT GTTTGCATCC GAATCGTGGT CTCGCTGTTC CTTGGGAGGG   720

TCTCCTCTGA GTGATTGACT ACCCACGACG GGGGTCTTTC ATTTGGGGGC TCGTCCGGGA   780

TTTGGAGACC CCTGCCCAGG GACCACCGAC CCACCACCGG GAGGTAAGCT GGCCAGCAAC   840

TTATCTGTGT CTGTCCGATT GTCTAGTGTC TATGTTTGAT GTTATGCGCC TGCGTCTGTA   900

CTAGTTAGCT AACTAGCTCT GTATCTGGCG GACCCGTGGT GGAACTGACG AGTTCTGAAC   960

ACCCGGCCGC AACCCTGGGA GACGTCCAG GGACTTTGGG GGCCGTTTTT GTGGCCCGAC   1020

CTGAGGAAGG GAGTCGATGT GGAATCCGAC CCCGTCAGGA TATGTGGTTC TGGTAGGAGA  1080

CGAGAACCTA AACAGTTCC CGCCTCCGTC TGAATTTTTG CTTTCGGTTT GGAACCGAAG   1140

CCGCGCGTCT TGTCTGCTGC AGCATCGTTC TGTGTTGTCT CTGTCTGACT GTGTTTCTGT  1200

ATTTGTCTGA AAATTAGGGC CAGACTGTTA CCACTCCCTT AAGTTTGACC TTAGGTCACT   1260

GGAAAGATGT CGAGCGGATC GCTCACAACC AGTCGGTAGA TGTCAAGAAG AGACGTTGGG   1320

TTACCTTCTG CTCTGCAGAA TGGCCAACCT TTAACGTCGG ATGGCCGCGA GACGGCACCT   1380
```

```
TTAACCGAGA CCTCATCACC CAGGTTAAGA TCAAGGTCTT TTCACCTGGC CCGCATGGAC  1440
ACCCAGACCA GGTCCCCTAC ATCGTGACCT GGGAAGCCTT GGCTTTTGAC CCCCCTCCCT  1500
GGGTCAAGCC CTTTGTACAC CCTAAGCCTC CGCCTCCTCT TCCTCCATCC GCCCCGTCTC  1560
TCCCCCTTGA ACCTCCTCGT TCGACCCCGC CTCGATCCTC CCTTTATCCA GCCCTCACTC  1620
CTTCTCTAGG CGCCGGAATT GATCCGGAC  CATGAGCTTC AATACCCTGA TTGACTGGAA  1680
CAGCTGTAGC CCTGAACAGC AGCGTGCGCT GCTGACGCGT CCGGCGATTT CCGCCTCTGA  1740
CAGTATTACC CGGACGGTCA GCGATATTCT GGATAATGTA AAAACGCGCG GTGACGATGC  1800
CCTGCGTGAA TACAGCGCTA AATTTGATAA AACAGAAGTG ACAGCGCTAC GCGTCACCCC  1860
TGAAGAGATC GCCGCCGCCG GCGCGCGTCT GAGCGACGAA TTAAAACAGG CGATGACCGC  1920
TGCCGTCAAA AATATTGAAA CGTTCCATTC CGCGCAGACG CTACCGCCTG TAGATGTGGA  1980
AACCCAGCCA GGCGTGCGTT GCCAGCAGGT TACGCGTCCC GTCTCGTCTG TCGGTCTGTA  2040
TATTCCCGGC GGCTCGGCTC CGCTCTTCTC AACGGTGCTG ATGCTGGCGA CGCCGGCGCG  2100
CATTGCGGGA TGCCAGAAGG TGGTTCTGTG CTCGCCGCCG CCCATCGCTG ATGAAATCCT  2160
CTATGCGGCG CAACTGTGTG GCGTGCAGGA ATCTTTAAC  GTCGGCGGCG CGCAGGCGAT  2220
TGCCGCTCTG GCCTTCGGCA GCGAGTCCGT ACCGAAAGTG GATAAATTT  TTGGCCCCGG  2280
CAACGCCTTT GTAACCGAAG CCAAACGTCA GGTCAGCCAG CGTCTCGACG GCGCGGCTAT  2340
CGATATGCCA GCCGGGCCGT CTGAAGTACT GGTGATCGCA GACAGCGGCG CAACACCGGA  2400
TTTCGTCGCT TCTGACCTGC TCTCCCAGGC TGAGCACGGC CCGGATTCCC AGGTGATCCT  2460
GCTGACGCCT GATGCTGACA TTGCCCGCAA GGTGGCGGAG GCGGTAGAAC GTCAACTGGC  2520
GGAACTGCCG CGCGCGGACA CCGCCCGGCA GGCCCTGAGC GCCAGTCGTC TGATTGTGAC  2580
CAAAGATTTA GCGCAGTGCG TCGCCATCTC TAATCAGTAT GGGCCGGAAC ACTTAATCAT  2640
CCAGACGCGC AATGCGCGCG ATTTGGTGGA TGCGATTACC AGCGCAGGCT CGGTATTTCT  2700
CGGCGACTGG TCGCCGGAAT CCGCCGGTGA TTACGCTTCC GGAACCAACC ATGTTTTACC  2760
GACCTATGGC TATACTGCTA CCTGTTCCAG CCTTGGGTTA GCGGATTTCC AGAAACGGAT  2820
GACCGTTCAG GAACTGTCGA AAGCGGGCTT TTCCGCTCTG CATCAACCA  TTGAAACATT  2880
GGCGGCGGCA GAACGTCTGA CCGCCCATAA AAATGCCGTG ACCCTGCGCG TAAACGCCCT  2940
CAAGGAGCAA GCATGAGCAC TGAAAACACT CTCAGCGTCG CCGGGATCAA TTCGTTAACT  3000
CGAGGATCGG CCCAGCCACC AGGATGGTAT AGTATAGNAT AGATTTTATT TAGAGCATAG  3060
GGAGGGGAGT CAAGAGGGCA GTAGAGGCAA AGAAAGGAAG AGAGAGGGGG AGAGAAGAGA  3120
AGTAGAGGTG TAGAGGCTGG CCTTGGAGCA CGTGGAGAGA GCAGGGNAAA GGAATGGGGA  3180
GAGAGGGNAG AATTGGAAAC AGAGAAAGAG CAAGAGAGGA TCAAGAGAGC AAGGAGGGGG  3240
GCAAGCAGCC CNTTTTATAG TGAGTCAGGC ACACCTGGTT GTTGCCAGGT AACTGTGGGG  3300
CGGGGNTTAG ACACAAAGCT AAAAACATCC ACCACCTAGT TNATCTGCCA GACTCTCAAG  3360
GTCCTCGCAT ACCAGAGCCT GGGGGAATCC CAGAGGGAGA CATGTGAAGG CTCCCTGGGA  3420
CCCTGGTCAG GACNGGACCA TGTCTGTGCC CAGCCNGAGT TCCTCTAGGT CAGCCTAAAT  3480
TGGCCAGATC TACACTTGGT GGCAGGCAGT TTCAGGCTTT CTGGGAAGCA AAACTGGCAG  3540
AGAACAGAGC AGGATCCTTG AGTTGGGAAA GGAAAGTCTA GGGCCAGAGA CTGAACCTGG  3600
GGCTGGTCCT GTTCCACCTG TNCTCCNGT  GGTTTCATCC TCCAGTCCTT CAGCCCCTA   3660
GACCCAAGCC AGCCATGCAG CCCGCAGTAG CAAAGTAAGA GGCCACAGGT CCAGACTGGG  3720
TAGGGCAGAG GTGCCTGAGG CTTGGGGCAG GTGCTAGTTG GATCCGGTTT CCAGAGGCAA  3780
TATATATATA AAGGCTGCTG TTTCCCCGAT GGTGCAACAC CCCAGAGGCC TAGCCAGACC  3840
```

```
AACATTCCTG CCNAAAAGCC AGCTCTCCAT TTATAGCACC TTGGAAGACT AGCCAAGGGA 3900
GCTGAAATGC AAGGCCTGGA AAGGACAGGG GGAAATCAAA GGGCCACCTA TGGCGGCAGG 3960
AGAACTGAGC CTCAGGATGA GCTGTGTGCT TCTCCAGGTC AGTGGGCCTA CAGCCTAAGA 4020
GGCCCTGCAT TGAGGGGACA ATGCCTCAGC CCAGAGCCAA TGGCACGCTC CAGAAGGGGT 4080
GGCTGGGGGA AGTTTTAGTG ACCATAAAAT AAAAAGCAAG GTTGCAATCA CTTAGACTCA 4140
GCATAAAATT TATTTCGGTT TTTNTAAATT ATTCGTTTTG TTATTTGTGT GCTTGCTTTG 4200
CTTTGCTTTG TTTGCTCGGG TTTGAGATAA GAGAGAGAGA GAGAGAGAGA GAGAGAGAGA 4260
GAGGGAAGGA GGGAGGGAGG GAGGGAGGGA GGGAGGGAGG AAGGAAGGAA GGAAGGAAGG 4320
AAGGAAGAAA GAAAGAAAGA AGAAAGAAA GAAAGAAAGA AGAAAGAAA GAAAGAAACT 4380
AGATTTGCAC AAGTGGTTTG AAGTGCCTTC CTTGGAGACA CCAGGCACTG CATAATGAAA 4440
CAGACTTGCT CATTCATCNG CCGAAGGAAT ATTTGTGGTG CACCTAGAGA GAGCTGAGCA 4500
TATTCAGCTG AGGTTCCAAA AAGGAGGAAG CAATAGCTTC GATCGAAATC ATTACTAACG 4560
ACAATTACAT CCATCNCTGT AGATTTAAGT CAAATGAAAG AGCACTTATG ATGAACCCCA 4620
CATCCATCGG CAGCATACTG TTGGAATGTT GCAACCGACC AATGGGAGAG AGCACGTCCC 4680
AGGCAAACCA GCCTCTGCTT TGCCTGGGCA GAGGCAGCGT GAGAGCTTGT ATGAGTAAGT 4740
ACCTACATAG AGCCCAGGTT TGCTGGAATA GAATGACTTG TAGCACATTT TGCTAAATTC 4800
AAGTATAAGG ATAGAAATCA AAAGAGCCCA AGACTGTTCA TTCACTCGCT TGACACTTAA 4860
ACCACTGTGC CCGCCGTGGG ATCACTGCTG CAGTGGCTTC CGGACACGCC ATGGTGAGCA 4920
AAGTACTCCT ATCCATGGTA TGCTGGTCTT CGTGTCCCTC GGTGATAACT GACAAGATCA 4980
TTCTCGAGGT AGACACTGGA GAGGCTTGGG CAGGCTGCAC CAGATAGCCA AGTGCTACCG 5040
CGTATGGCTG CCAGTCTCTC TGCCCTCCTT CCTAGCTAGG CAGCTGCCCC AGCACAGAGT 5100
CGCGGGAGGG GGCACTCCCT GGCCCCAGTG GCTACCCTGG GACCCCAAG CTCCGCCCTA 5160
CTACACTCCT ATTGGCTTGA GGCGCCCCG CCCCCAGCCT CCCTTTCCAG CTCCCGGGCT 5220
TTTAGGCTAC CCTGGATAAA TAGCCCAGAG CTTGGGCTGC AGGTCGAGGC GGATCTGATC 5280
AAGAGACAGG ATGAGGATCG TTTCGCATGA TTGAACAAGA TGGATTGCAC GCAGGTTCTC 5340
CGGCCGCTTG GGTGGAGAGG CTATTCGGCT ATGACTGGGC ACAACAGACA ATCGGCTGCT 5400
CTGATGCCGC CGTGTTCCGG CTGTCAGCGC AGGGGCGCCC GGTTCTTTTT GTCAAGACCG 5460
ACCTGTCCGG TGCCCTGAAT GAACTGCAGG ACGAGGCAGC GCGGCTATCG TGGCTGGCCA 5520
CGACGGGCGT TCCTTGCGCA GCTGTGCTCG ACGTTGTCAC TGAAGCGGGA AGGGACTGGC 5580
TGCTATTGGG CGAAGTGCCG GGGCAGGATC TCCTGTCATC TCACCTTGCT CCTGCCGAGA 5640
AAGTATCCAT CATGGCTGAT GCAATGCGGC GGCTGCATAC GCTTGATCCG GCTACCTGCC 5700
CATTCGACCA CCAAGCGAAA CATCGCATCG AGCGAGCACG TACTCGGATG AAGCCGGTC 5760
TTGTCGATCA GGATGATCTG GACGAAGAGC ATCAGGGGCT CGCGCCAGCC GAACTGTTCG 5820
CCAGGCTCAA GGCGCGCATG CCCGACGGCG AGGATCTCGT CGTGACCCAT GGCGATGCCT 5880
GCTTGCCGAA TATCATGGTG GAAAATGGCC GCTTTTCTGG ATTCATCGAC TGTGGCCGGC 5940
TGGGTGTGGC GGACCGCTAT CAGGACATAG CGTTGGCTAC CCGTGATATT GCTGAAGAGC 6000
TTGGCGGCGA ATGGGCTGAC CGCTTCCTCG TGCTTTACGG TATCGCCGCT CCCGATTCGC 6060
AGCGCATCGC CTTCTATCGC CTTCTTGACG AGTTCTTCTG AGCGGGACTC TGGGGTTCGA 6120
TAAAATAAAA GATTTATTT AGTCTCCAGA AAAAGGGGGG AATGAAAGAC CCCACCTGTA 6180
GGTTTGGCAA GCTAGCTTAA GTAACGCCAT TTTGCAAGGC ATGGAAAAAT ACATAACTGA 6240
GAATAGAGAA GTTCAGATCA AGGTCAGGAA CAGATGGAAC AGCTGAATAT GGGCCAAACA 6300
```

```
GGATATCTGT GGTAAGCAGT TCCTGCCCCG GCTCAGGGCC AAGAACAGAT GGAACAGCTG  6360
AATATGGGCC AAACAGGATA TCTGTGGTAA GCAGTTCCTG CCCCGGCTCA GGGCCAAGAA  6420
CAGATGGTCC CCAGATGCGG TCCAGCCCTC AGCAGTTTCT AGAGAACCAT CAGATGTTTC  6480
CAGGGTGCCC CAAGGACCTG AAATGACCCT GTGCCTTATT TGAACTAACC AATCAGTTCG  6540
CTTCTCGCTT CTGTTCGCGC GCTTCTGCTC CCCGAGCTCA ATAAAGAGC  CCACAACCCC  6600
TCACTCGGGG CGCCAGTCCT CCGATTGACT GAGTCGCCCG GGTACCCGTG TATCCAATAA  6660
ACCCTCTTGC AGTTGCATCC GACTTGTGGT CTCGCTGTTC CTTGGGAGGG TCTCCTCTGA  6720
GTGATTGACT ACCCGTCAGC GGGGGTCTTT CATTTGGGGG CTCGTCCGGG ATCGGGAGAC  6780
CCCTGCCCAG GGACCACCGA CCCACCACCG GGAGGTAAGC TGGCTGCCTC GCGCGTTTCG  6840
GTGATGACGG TGAAAACCTC TGACACATGC AGCTCCCGGA GACGGTCACA GCTTGTCTGT  6900
AAGCGGATGC CGGGAGCAGA CAAGCCCGTC AGGGCGCGTC AGCGGGTGTT GGCGGGTGTC  6960
GGGGCGCAGC CATGACCCAG TCACGTAGCG ATAGCGGAGT GTATACTGGC TTAACTATGC  7020
GGCATCAGAG CAGATTGTAC TGAGAGTGCA CCATATGCGG TGTGAAATAC CGCACAGATG  7080
CGTAAGGAGA AAATACCGCA TCAGGCGCTC TTCCGCTTCC TCGCTCACTG ACTCGCTGCG  7140
CTCGGTCGTT CGGCTGCGGC GAGCGGTATC AGCTCACTCA AAGGCGGTAA TACGGTTATC  7200
CACAGAATCA GGGGATAACG CAGGAAAGAA CATGTGAGCA AAAGGCCAGC AAAAGGCCAG  7260
GAACCGTAAA AAGGCCGCGT TGCTGGCGTT TTTCCATAGG CTCCGCCCCC CTGACGAGCA  7320
TCACAAAAAT CGACGCTCAA GTCAGAGGTG GCGAAACCCG ACAGGACTAT AAAGATACCA  7380
GGCGTTTCCC CCTGGAAGCT CCCTCGTGCG CTCTCCTGTT CCGACCCTGC CGCTTACCGG  7440
ATACCTGTCC GCCTTTCTCC CTTCGGGAAG CGTGGCGCTT TCTCATAGCT CACGCTGTAG  7500
GTATCTCAGT TCGGTGTAGG TCGTTCGCTC CAAGCTGGGC TGTGTGCACG AACCCCCCGT  7560
TCAGCCCGAC CGCTGCGCCT TATCCGGTAA CTATCGTCTT GAGTCCAACC CGGTAAGACA  7620
CGACTTATCG CCACTGGCAG CAGCCACTGG TAACAGGATT AGCAGAGCGA GGTATGTAGG  7680
CGGTGCTACA GAGTTCTTGA AGTGGTGGCC TAACTACGGC TACACTAGAA GGACAGTATT  7740
TGGTATCTGC GCTCTGCTGA AGCCAGTTAC CTTCGGAAAA AGAGTTGGTA GCTCTTGATC  7800
CGGCAAACAA ACCACCGCTG GTAGCGGTGG TTTTTTTGTT TGCAAGCAGC AGATTACGCG  7860
CAGAAAAAAA GGATCTCAAG AAGATCCTTT GATCTTTTCT ACGGGGTCTG ACGCTCAGTG  7920
GAACGAAAAC TCACGTTAAG GGATTTTGGT CATGAGATTA TCAAAAGGA  TCTTCACCTA  7980
GATCCTTTTA AATTAAAAAT GAAGTTTTAA ATCAATCTAA AGTATATATG AGTAAACTTG  8040
GTCTGACAGT TACCAATGCT TAATCAGTGA GGCACCTATC TCAGCGATCT GTCTATTTCG  8100
TTCATCCATA GTTGCCTGAC TCCCCGTCGT GTAGATAACT ACGATACGGG AGGGCTTACC  8160
ATCTGGCCCC AGTGCTGCAA TGATACCGCG AGACCCACGC TCACCGGCTC CAGATTTATC  8220
AGCAATAAAC CAGCCAGCCG GAAGGGCCGA GCGCAGAAGT GGTCCTGCAA CTTTATCCGC  8280
CTCCATCCAG TCTATTAATT GTTGCCGGGA AGCTAGAGTA AGTAGTTCGC CAGTTAATAG  8340
TTTGCGCAAC GTTGTTGCCA TTGCTGCAGG CATCGTGGTG TCACGCTCGT CGTTTGGTAT  8400
GGCTTCATTC AGCTCCGGTT CCCAACGATC AAGGCGAGTT ACATGATCCC CCATGTTGTG  8460
CAAAAAAGCG GTTAGCTCCT TCGGTCCTCC GATCGTTGTC AGAAGTAAGT TGGCCGCAGT  8520
GTTATCACTC ATGGTTATGG CAGCACTGCA TAATTCTCTT ACTGTCATGC CATCCGTAAG  8580
ATGCTTTTCT GTGACTGGTG AGTACTCAAC CAAGTCATTC TGAGAATAGT GTATGCGGCG  8640
ACCGAGTTGC TCTTGCCCGG CGTCAACACG GATAATACC  GCGCCACATA GCAGAACTTT  8700
AAAAGTGCTC ATCATTGGAA AACGTTCTTC GGGGCGAAAA CTCTCAAGGA TCTTACCGCT  8760
```

| | | | | | |
|---|---|---|---|---|---|
|GTTGAGATCC|AGTTCGATGT|AACCCACTCG|TGCACCCAAC|TGATCTTCAG|CATCTTTTAC 8820|
|TTTCACCAGC|GTTTCTGGGT|GAGCAAAAAC|AGGAAGGCAA|AATGCCGCAA|AAAAGGGAAT 8880|
|AAGGGCGACA|CGGAAATGTT|GAATACTCAT|ACTCTTCCTT|TTTCAATATT|ATTGAAGCAT 8940|
|TTATCAGGGT|TATTGTCTCA|TGAGCGGATA|CATATTTGAA|TGTATTTAGA|AAAATAAACA 9000|
|AATAGGGGTT|CCGCGCACAT|TTCCCCGAAA|AGTGCCACCT|GACGTCTAAG|AAACCATTAT 9060|
|TATCATGACA|TTAACCTATA|AAAATAGGCG|TATCACGAGG|CCCTTTCGTC|TTCAA 9115|

(2) INFORMATION FOR SEQ ID NO:4:

(i) SEQUENCE CHARACTERISTICS:
　　　　(A) LENGTH:8316 base pairs
　　　　(B) TYPE:nucleic acid
　　　　(C) STRANDEDNESS:single
　　　　(D) TOPOLOGY:linear (ii) MOLECULE TYPE:Other;plasmid DNA
　　　　(A) DESCRIPTION:pLHDMDN-NSA: 5'LTR (position 1-1159);
　　　　　　y (position 1160- 1640); HisD (position 1641-2928),
　　　　　　Myo-D NSA ApaI fragment (position 2929-4389);
　　　　　　driving neo (position 4390-5259); with 3'LTR
　　　　　　(position 5260-5964); Figures 8A-8C.

(ix) SEQUENCE DESCRIPTION: SEQ ID NO:4:

| | | | | | |
|---|---|---|---|---|---|
|GAATTGCTAG|CAATTGCTAG|CAATTGCTAG|CAATTCATAC|CAGATCACCG|AAAACTGTCC 60|
|TCCAAATGTG|TCCCCCTCAC|ACTCCCAAAT|TCGCGGGCTT|CTGCCTCTTA|GACCACTCTA 120|
|CCCTATTCCC|CACACTCACC|GGAGCCAAAG|CCGCGGCCCT|TCCGTTTCTT|TGCTTTTGAA 180|
|AGACCCCACC|CGTAGGTGGC|AAGCTAGCTT|AAGTAACGCC|ACTTTGCAAG|GCATGGAAAA 240|
|ATACATAACT|GAGAATAGGA|AAGTTCAGAT|CAAGGTCAGG|AACAAAGAAA|CAGCTGAATA 300|
|CCAAACAGGA|TATCTGTGGT|AAGCGGTTCC|TGCCCCGGCT|CAGGGCCAAG|AACAGATGAG 360|
|ACAGCTGAGT|GATGGGCCAA|ACAGGATATC|TGTGGTAAGC|AGTTCCTGCC|CCGGCTCGGG 420|
|GCCAAGAACA|GATGGTCCCC|AGATGCGGTC|CAGCCCTCAG|CAGTTTCTAG|TGAATCATCA 480|
|GATGTTTCCA|GGGTGCCCCA|AGGACCTGAA|AATGACCCTG|TACCTTATTT|GAACTAACCA 540|
|ATCAGTTCGC|TTCTCGCTTC|TGTTCGCGCG|CTTCCGCTCT|CCGAGCTCAA|TAAAAGAGCC 600|
|CACAACCCCT|CACTCGGCGC|GCCAGTCTTC|CGATAGACTG|CGTCGCCCGG|GTACCCGTAT 660|
|TCCCAATAAA|GCCTCTTGCT|GTTTGCATCC|GAATCGTGGT|CTCGCTGTTC|CTTGGGAGGG 720|
|TCTCCTCTGA|GTGATTGACT|ACCCACGACG|GGGGTCTTTC|ATTTGGGGGC|TCGTCCGGGA 780|
|TTTGGAGACC|CCTGCCCAGG|GACCACCGAC|CCACCACCGG|GAGGTAAGCT|GGCCAGCAAC 840|
|TTATCTGTGT|CTGTCCGATT|GTCTAGTGTC|TATGTTTGAT|GTTATGCGCC|TGCGTCTGTA 900|
|CTAGTTAGCT|AACTAGCTCT|GTATCTGGCG|GACCCGTGGT|GGAACTGACG|AGTTCTGAAC 960|
|ACCCGGCCGC|AACCCTGGGA|GACGTCCCAG|GGACTTTGGG|GGCCGTTTTT|GTGGCCCGAC 1020|
|CTGAGGAAGG|GAGTCGATGT|GGAATCCGAC|CCCGTCAGGA|TATGTGGTTC|TGGTAGGAGA 1080|
|CGAGAACCTA|AAACAGTTCC|CGCCTCCGTC|TGAATTTTTG|CTTTCGGTTT|GGAACCGAAG 1140|
|CCGCGCGTCT|TGTCTGCTGC|AGCATCGTTC|TGTGTTGTCT|CTGTCTGACT|GTGTTTCTGT 1200|
|ATTTGTCTGA|AAATTAGGGC|CAGACTGTTA|CCACTCCCTT|AAGTTTGACC|TTAGGTCACT 1260|
|GGAAAGATGT|CGAGCGGATC|GCTCACAACC|AGTCGGTAGA|TGTCAAGAAG|AGACGTTGGG 1320|
|TTACCTTCTG|CTCTGCAGAA|TGGCCAACCT|TTAACGTCGG|ATGGCCGCGA|GACGGCACCT 1380|
|TTAACCGAGA|CCTCATCACC|CAGGTTAAGA|TCAAGGTCTT|TTCACCTGGC|CCGCATGGAC 1440|
|ACCCAGACCA|GGTCCCCTAC|ATCGTGACCT|GGGAAGCCTT|GGCTTTTGAC|CCCCCTCCCT 1500|
|GGGTCAAGCC|CTTTGTACAC|CCTAAGCCTC|CGCCTCCTCT|TCCTCCATCC|GCCCCGTCTC 1560|

```
TCCCCCTTGA  ACCTCCTCGT  TCGACCCCGC  CTCGATCCTC  CCTTTATCCA  GCCCTCACTC  1620
CTTCTCTAGG  CGCCGGAATT  GATCCCGGAC  CATGAGCTTC  AATACCCTGA  TTGACTGGAA  1680
CAGCTGTAGC  CCTGAACAGC  AGCGTGCGCT  GCTGACGCGT  CCGGCGATTT  CCGCCTCTGA  1740
CAGTATTACC  CGGACGGTCA  GCGATATTCT  GGATAATGTA  AAAACGCGCG  GTGACGATGC  1800
CCTGCGTGAA  TACAGCGCTA  AATTTGATAA  AACAGAAGTG  ACAGCGCTAC  GCGTCACCCC  1860
TGAAGAGATC  GCCGCCGCCG  GCGCGCGTCT  GAGCGACGAA  TTAAAACAGG  CGATGACCGC  1920
TGCCGTCAAA  AATATTGAAA  CGTTCCATTC  CGCGCAGACG  CTACCGCCTG  TAGATGTGGA  1980
AACCCAGCCA  GGCGTGCGTT  GCCAGCAGGT  TACGCGTCCC  GTCTCGTCTG  TCGGTCTGTA  2040
TATTCCCGGC  GGCTCGGCTC  CGCTCTTCTC  AACGGTGCTG  ATGCTGGCGA  CGCCGGCGCG  2100
CATTGCGGGA  TGCCAGAAGG  TGGTTCTGTG  CTCGCCGCCG  CCCATCGCTG  ATGAAATCCT  2160
CTATGCGGCG  CAACTGTGTG  GCGTGCAGGA  AATCTTTAAC  GTCGGCGGCG  CGCAGGCGAT  2220
TGCCGCTCTG  GCCTTCGGCA  GCGAGTCCGT  ACCGAAAGTG  GATAAATTT   TTGGCCCCGG  2280
CAACGCCTTT  GTAACCGAAG  CCAAACGTCA  GGTCAGCCAG  CGTCTCGACG  GCGCGGCTAT  2340
CGATATGCCA  GCCGGGCCGT  CTGAAGTACT  GGTGATCGCA  GACAGCGGCG  CAACACCGGA  2400
TTTCGTCGCT  TCTGACCTGC  TCTCCCAGGC  TGAGCACGGC  CCGGATTCCC  AGGTGATCCT  2460
GCTGACGCCT  GATGCTGACA  TTGCCCGCAA  GGTGGCGGAG  GCGGTAGAAC  GTCAACTGGC  2520
GGAACTGCCG  CGCGCGGACA  CCGCCCGGCA  GGCCCTGAGC  GCCAGTCGTC  TGATTGTGAC  2580
CAAAGATTTA  GCGCAGTGCG  TCGCCATCTC  TAATCAGTAT  GGGCCGGAAC  ACTTAATCAT  2640
CCAGACGCGC  AATGCGCGCG  ATTTGGTGGA  TGCGATTACC  AGCGCAGGCT  CGGTATTTCT  2700
CGGCGACTGG  TCGCCGGAAT  CCGCCGGTGA  TTACGCTTCC  GGAACCAACC  ATGTTTTACC  2760
GACCTATGGC  TATACTGCTA  CCTGTTCCAG  CCTTGGGTTA  GCGGATTTCC  AGAAACGGAT  2820
GACCGTTCAG  GAACTGTCGA  AAGCGGGCTT  TTCCGCTCTG  GCATCAACCA  TTGAAACATT  2880
GGCGGCGGCA  GAACGTCTGA  CCGCCCATAA  AAATGCCGTG  ACCCTGCGCG  TAAACGCCCT  2940
CAAGGAGCAA  GCATGAGCAC  TGAAAACACT  CTCAGCGTCG  CCGGGATCAA  TTCGTTAACT  3000
CGAGGATCGG  CCCAGCCACC  AGGATGGTAT  AGTATAGNAT  AGATTTTATT  TAGAGCATAG  3060
GGAGGGGAGT  CAAGAGGGCA  GTAGAGGCAA  AGAAAGGAAG  AGAGAGGGGG  AGAGAAGAGA  3120
AGTAGAGGTG  TAGAGGCTGG  CCTTGGAGCA  CGTGGAGAGA  GCAGGGAAA   GGAATGGGGA  3180
GAGAGGGNAG  AATTGGAAAC  AGAGAAAGAG  CAAGAGAGGA  TCAAGAGAGC  AAGGAGGGGG  3240
GCAAGCAGCC  CNTTTTATAG  TGAGTCAGGC  ACACCTGGTT  GTTGCCAGGT  AACTGTGGGG  3300
CGGGGNTTAG  ACACAAAGCT  AAAAACATCC  ACCACCTAGT  TNATCTGCCA  GACTCTCAAG  3360
GTCCTCGCAT  ACCAGAGCCT  GGGGGAATCC  CAGAGGGAGA  CATGTGAAGG  CTCCCTGGGA  3420
CCCTGGTCAG  GACNGGACCA  TGTCTGTGCC  CAGCCNGAGT  TCCTCTAGGT  CAGCCTAAAT  3480
TGGCCAGATC  TACACTTGGT  GGCAGGCAGT  TTCAGGCTTT  CTGGGAAGCA  AAACTGGCAG  3540
AGAACAGAGC  AGGATCCTTG  AGTTGGGAAA  GGAAAGTCTA  GGCCAGAGA   CTGAACCTGG  3600
GGCTGGTCCT  GTTCCACCTG  TNCTCCCNGT  GGTTTCATCC  TCCAGTCCTT  CAGCCCCCTA  3660
GACCCAAGCC  AGCCATGCAG  CCCGCAGTAG  CAAAGTAAGA  GGCCACAGGT  CCAGACTGGG  3720
TAGGGCAGAG  GTGCCTGAGG  CTTGGGGCAG  GTGCTAGTTG  GATCCGGTTT  CCAGAGGCAA  3780
TATATATATA  AAGGCTGCTG  TTTCCCCGAT  GGTGCAACAC  CCCAGAGGCC  TAGCCAGACC  3840
AACATTCCTG  CCNAAAAGCC  AGCTCTCCAT  TTATAGCACC  TTGGAAGACT  AGCCAAGGGA  3900
GCTGAAATGC  AAGGCCTGGA  AAGGACAGGG  GGAAATCAAA  GGGCCACCTA  TGGCGGCAGG  3960
AGAACTGAGC  CTCAGGATGA  GCTGTGTGCT  TCTCCAGGTC  AGTGGGCCTA  CAGCCTAAGA  4020
```

```
GGCCCTGCAT TGAGGGGACA ATGCCTCAGC CCAGAGCCAA TGGCACGCTC CAGAAGGGGT     4080
GGCTGGGGGA AGTTTTAGTG ACCATAAAAT AAAAAGCAAG GTTGCAATCA CTTAGACTCA     4140
GCATAAAATT TATTTCGGTT TTTNTAAATT ATTCGTTTTG TTATTTGTGT GCTTGCTTTG     4200
CTTTGCTTTG TTTGCTCGGN GTAGACACTG GAGAGGCTTG GCAGGCTGC ACCAGATAGC      4260
CAAGTGCTAC CGCGTATGGC TGCCAGTCTC TCTGCCCTCC TTCCTAGCTA GGCAGCTGCC     4320
CCAGCACAGA GTCGCGGGAG GGGGCACTCC CTGGCCCCAG TGGCTACCCT GGGGACCCCA     4380
AGCTCCGCCC TACTACACTC CTATTGGCTT GAGGCGGGGC TTTTAGGCTA CCCTGGATAA     4440
ATAGCCCAGA GCTTGGGCTG CAGGTCGAGG CGGATCTGAT CAAGAGACAG GATGAGGATC     4500
GTTTCGCATG ATTGAACAAG ATGGATTGCA CGCAGGTTCT CCGGCCGCTT GGGTGGAGAG     4560
GCTATTCGGC TATGACTGGG CACAACAGAC AATCGGCTGC TCTGATGCCG CCGTGTTCCG     4620
GCTGTCAGCG CAGGGGCGCC CGGTTCTTTT TGTCAAGACC GACCTGTCCG GTGCCCTGAA     4680
TGAACTGCAG GACGAGGCAG CGCGGCTATC GTGGCTGGCC ACGACGGGCG TTCCTTGCGC     4740
AGCTGTGCTC GACGTTGTCA CTGAAGCGGG AAGGGACTGG CTGCTATTGG GCGAAGTGCC     4800
GGGGCAGGAT CTCCTGTCAT CTCACCTTGC TCCTGCCGAG AAAGTATCCA TCATGGCTGA     4860
TGCAATGCGG CGGCTGCATA CGCTTGATCC GGCTACCTGC CCATTCGACC ACCAAGCGAA     4920
ACATCGCATC GAGCGAGCAC GTACTCGGAT GGAAGCCGGT CTTGTCGATC AGGATGATCT     4980
GGACGAAGAG CATCAGGGGC TCGCGCCAGC CGAACTGTTC GCCAGGCTCA AGGCGCGCAT     5040
GCCCGACGGC GAGGATCTCG TCGTGACCCA TGGCGATGCC TGCTTGCCGA ATATCATGGT     5100
GGAAAATGGC CGCTTTTCTG GATTCATCGA CTGTGGCCGG CTGGGTGTGG CGGACCGCTA     5160
TCAGGACATA GCGTTGGCTA CCCGTGATAT TGCTGAAGAG CTTGGCGGCG AATGGGCTGA     5220
CCGCTTCCTC GTGCTTTACG GTATCGCCGC TCCCGATTCG CAGCGCATCG CCTTCTATCG     5280
CCTTCTTGAC GAGTTCTTCT GAGCGGGACT CTGGGGTTCG ATAAAATAAA AGATTTTATT     5340
TAGTCTCCAG AAAAAGGGGG GAATGAAAGA CCCCACCTGT AGGTTTGGCA AGCTAGCTTA     5400
AGTAACGCCA TTTTGCAAGG CATGGAAAAA TACATAACTG AGAATAGAGA AGTTCAGATC     5460
AAGGTCAGGA ACAGATGGAA CAGCTGAATA TGGGCCAAAC AGGATATCTG TGGTAAGCAG     5520
TTCCTGCCCC GGCTCAGGGC CAAGAACAGA TGGAACAGCT GAATATGGGC CAAACAGGAT     5580
ATCTGTGGTA AGCAGTTCCT GCCCCGGCTC AGGGCCAAGA ACAGATGGTC CCCAGATGCG     5640
GTCCAGCCCT CAGCAGTTTC TAGAGAACCA TCAGATGTTT CCAGGGTGCC CCAAGGACCT     5700
GAAATGACCC TGTGCCTTAT TTGAACTAAC CAATCAGTTC GCTTCTCGCT TCTGTTCGCG     5760
CGCTTCTGCT CCCCGAGCTC AATAAAAGAG CCCACAACCC CTCACTCGGG GCGCCAGTCC     5820
TCCGATTGAC TGAGTCGCCC GGGTACCCGT GTATCCAATA AACCCTCTTG CAGTTGCATC     5880
CGACTTGTGG TCTCGCTGTT CCTTGGGAGG GTCTCCTCTG AGTGATTGAC TACCCGTCAG     5940
CGGGGGTCTT TCATTTGGGG GCTCGTCCGG GATCGGGAGA CCCCTGCCCA GGGACCACCG     6000
ACCCACCACC GGGAGGTAAG CTGGCTGCCT CGCGCGTTTC GGTGATGACG GTGAAAACCT     6060
CTGACACATG CAGCTCCCGG AGACGGTCAC AGCTTGTCTG TAAGCGGATG CCGGGAGCAG     6120
ACAAGCCCGT CAGGGCGCGT CAGCGGGTGT TGGCGGGTGT CGGGGCGCAG CCATGACCCA     6180
GTCACGTAGC GATAGCGGAG TGTATACTGG CTTAACTATG CGGCATCAGA GCAGATTGTA     6240
CTGAGAGTGC ACCATATGCG GTGTGAAATA CCGCACAGAT GCGTAAGGAG AAAATACCGC     6300
ATCAGGCGCT CTTCCGCTTC CTCGCTCACT GACTCGCTGC GCTCGGTCGT TCGGCTGCGG     6360
CGAGCGGTAT CAGCTCACTC AAAGGCGGTA ATACGGTTAT CCACAGAATC AGGGGATAAC     6420
GCAGGAAAGA ACATGTGAGC AAAAGGCCAG CAAAAGGCCA GGAACCGTAA AAAGGCCGCG     6480
```

```
TTGCTGGCGT TTTTCCATAG GCTCCGCCCC CCTGACGAGC ATCACAAAAA TCGACGCTCA    6540
AGTCAGAGGT GGCGAAACCC GACAGGACTA TAAAGATACC AGGCGTTTCC CCCTGGAAGC    6600
TCCCTCGTGC GCTCTCCTGT TCCGACCCTG CCGCTTACCG GATACCTGTC CGCCTTTCTC    6660
CCTTCGGGAA GCGTGGCGCT TTCTCATAGC TCACGCTGTA GGTATCTCAG TTCGGTGTAG    6720
GTCGTTCGCT CCAAGCTGGG CTGTGTGCAC GAACCCCCCG TTCAGCCCGA CCGCTGCGCC    6780
TTATCCGGTA ACTATCGTCT TGAGTCCAAC CCGGTAAGAC ACGACTTATC GCCACTGGCA    6840
GCAGCCACTG GTAACAGGAT TAGCAGAGCG AGGTATGTAG GCGGTGCTAC AGAGTTCTTG    6900
AAGTGGTGGC CTAACTACGG CTACACTAGA AGGACAGTAT TTGGTATCTG CGCTCTGCTG    6960
AAGCCAGTTA CCTTCGGAAA AAGAGTTGGT AGCTCTTGAT CCGGCAAACA AACCACCGCT    7020
GGTAGCGGTG GTTTTTTTGT TTGCAAGCAG CAGATTACGC GCAGAAAAA  AGGATCTCAA    7080
GAAGATCCTT TGATCTTTTC TACGGGGTCT GACGCTCAGT GGAACGAAAA CTCACGTTAA    7140
GGGATTTTGG TCATGAGATT ATCAAAAAGG ATCTTCACCT AGATCCTTTT AAATTAAAAA    7200
TGAAGTTTTA AATCAATCTA AAGTATATAT GAGTAAACTT GGTCTGACAG TTACCAATGC    7260
TTAATCAGTG AGGCACCTAT CTCAGCGATC TGTCTATTTC GTTCATCCAT AGTTGCCTGA    7320
CTCCCCGTCG TGTAGATAAC TACGATACGG GAGGGCTTAC CATCTGGCCC CAGTGCTGCA    7380
ATGATACCGC GAGACCCACG CTCACCGGCT CCAGATTTAT CAGCAATAAA CCAGCCAGCC    7440
GGAAGGGCCG AGCGCAGAAG TGGTCCTGCA ACTTTATCCG CCTCCATCCA GTCTATTAAT    7500
TGTTGCCGGG AAGCTAGAGT AAGTAGTTCG CCAGTTAATA GTTTGCGCAA CGTTGTTGCC    7560
ATTGCTGCAG GCATCGTGGT GTCACGCTCG TCGTTTGGTA TGGCTTCATT CAGCTCCGGT    7620
TCCCAACGAT CAAGGCGAGT TACATGATCC CCCATGTTGT GCAAAAAGC  GGTTAGCTCC    7680
TTCGGTCCTC CGATCGTTGT CAGAAGTAAG TTGGCCGCAG TGTTATCACT CATGGTTATG    7740
GCAGCACTGC ATAATTCTCT TACTGTCATG CCATCCGTAA GATGCTTTTC TGTGACTGGT    7800
GAGTACTCAA CCAAGTCATT CTGAGAATAG TGTATGCGGC GACCGAGTTG CTCTTGCCCG    7860
GCGTCAACAC GGGATAATAC CGCGCCACAT AGCAGAACTT TAAAAGTGCT CATCATTGGA    7920
AAACGTTCTT CGGGGCGAAA ACTCTCAAGG ATCTTACCGC TGTTGAGATC CAGTTCGATG    7980
TAACCCACTC GTGCACCCAA CTGATCTTCA GCATCTTTTA CTTTCACCAG CGTTTCTGGG    8040
TGAGCAAAAA CAGGAAGGCA AAATGCCGCA AAAAAGGGAA TAAGGGCGAC ACGGAAATGT    8100
TGAATACTCA TACTCTTCCT TTTTCAATAT TATTGAAGCA TTTATCAGGG TTATTGTCTC    8160
ATGAGCGGAT ACATATTTGA ATGTATTTAG AAAAATAAAC AAATAGGGGT TCCGCGCACA    8220
TTTCCCCGAA AAGTGCCACC TGACGTCTAA GAAACCATTA TTATCATGAC ATTAACCTAT    8280
AAAAATAGGC GTATCACGAG GCCCTTTCGT CTTCAA                              8316
```